(12) United States Patent
Rapacki et al.

(10) Patent No.: US 11,951,038 B2
(45) Date of Patent: *Apr. 9, 2024

(54) LACRIMAL IMPLANTS AND RELATED METHODS

(71) Applicant: Mati Therapeutics Inc., Austin, TX (US)

(72) Inventors: Alan R. Rapacki, Redwood City, CA (US); Valery Rubinchik, Richmond (CA); John B. Holds, St. Louis, MO (US); Sylvie Sim, Mountain View, CA (US); Danny Shen, Stanford, CA (US)

(73) Assignee: Mati Therapeutics Inc., Austin, TX (US)

( * ) Notice: Subject to any disclaimer, the term of this patent is extended or adjusted under 35 U.S.C. 154(b) by 867 days.

This patent is subject to a terminal disclaimer.

(21) Appl. No.: 16/594,576

(22) Filed: Oct. 7, 2019

(65) Prior Publication Data

US 2020/0030144 A1 Jan. 30, 2020

Related U.S. Application Data

(60) Continuation of application No. 15/707,386, filed on Sep. 18, 2017, now Pat. No. 10,434,009, which is a
(Continued)

(51) Int. Cl.
*A61F 9/00* (2006.01)
*A61F 9/007* (2006.01)

(52) U.S. Cl.
CPC ........ *A61F 9/0017* (2013.01); *A61F 9/00772* (2013.01); *A61F 2210/0061* (2013.01); *A61F 2220/0008* (2013.01); *A61F 2250/0067* (2013.01); *Y10T 407/19* (2015.01); *Y10T 409/304256* (2015.01)

(58) Field of Classification Search
CPC ................ A61F 9/0017; A61F 9/00772; A61F 2210/0061; A61F 2220/0008; A61F 2250/0067
See application file for complete search history.

(56) References Cited

U.S. PATENT DOCUMENTS

| 3,865,108 A | 2/1975 | Hartop |
| 3,949,750 A | 4/1976 | Freeman |

(Continued)

FOREIGN PATENT DOCUMENTS

| EP | 0442745 A1 | 8/1991 |
| EP | 0621022 A1 | 10/1994 |

(Continued)

OTHER PUBLICATIONS

"European Application No. 08330451.4. Examination Report dated Nov. 5, 2010".
(Continued)

*Primary Examiner* — Philip R Wiest
(74) *Attorney, Agent, or Firm* — Koren Anderson

(57) ABSTRACT

Lacrimal implants for treating diseases or disorders are disclosed. More particularly, lacrimal implants, methods of making such implants, and methods of treating ocular, respiration, inner ear or other diseases or disorders using such implants are disclosed.

19 Claims, 26 Drawing Sheets

SECTION 3B-3B

Related U.S. Application Data continuation of application No. 15/247,703, filed on Aug. 25, 2016, now Pat. No. 9,763,824, which is a continuation of application No. 14/192,915, filed on Feb. 28, 2014, now Pat. No. 9,445,944, which is a continuation of application No. 13/598,201, filed on Aug. 29, 2012, now Pat. No. 8,702,643, which is a division of application No. 12/231,989, filed on Sep. 8, 2008, now Pat. No. 8,333,726.

(60) Provisional application No. 61/075,309, filed on Jun. 24, 2008, provisional application No. 61/052,595, filed on May 12, 2008, provisional application No. 61/049,360, filed on Apr. 30, 2008, provisional application No. 61/036,816, filed on Mar. 14, 2008, provisional application No. 61/033,211, filed on Mar. 3, 2008, provisional application No. 60/974,367, filed on Sep. 21, 2007, provisional application No. 60/970,696, filed on Sep. 7, 2007, provisional application No. 60/970,720, filed on Sep. 7, 2007.

(56) References Cited

U.S. PATENT DOCUMENTS

| | | |
|---|---|---|
| 4,014,335 A | 3/1977 | Arnold |
| 4,660,546 A | 4/1987 | Herrick et al. |
| 4,886,488 A | 12/1989 | White |
| 4,915,684 A | 4/1990 | MacKeen et al. |
| 4,959,048 A | 9/1990 | Seder et al. |
| 5,041,081 A | 8/1991 | Odrich |
| 5,049,142 A | 9/1991 | Herrick et al. |
| 5,053,030 A | 10/1991 | Herrick et al. |
| 5,128,058 A | 7/1992 | Ishil et al. |
| 5,133,159 A | 7/1992 | Nelson |
| 5,163,959 A | 11/1992 | Herrick |
| 5,171,270 A | 12/1992 | Herrick |
| 5,283,063 A | 2/1994 | Freeman |
| 5,318,513 A | 6/1994 | Leib et al. |
| 5,334,137 A | 8/1994 | Freeman |
| 5,395,618 A | 3/1995 | Darougar et al. |
| 5,417,651 A * | 5/1995 | Guena ............... A61F 9/00772 606/198 |
| 5,423,777 A | 6/1995 | Tajiri et al. |
| 5,466,233 A | 11/1995 | Weiner et al. |
| 5,556,633 A | 9/1996 | Haddad et al. |
| 5,707,643 A | 1/1998 | Ogura et al. |
| 5,723,005 A | 3/1998 | Herrick |
| 5,741,292 A | 4/1998 | Mendius |
| 5,766,243 A | 6/1998 | Christensen et al. |
| 5,773,019 A | 6/1998 | Ashton et al. |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano et al. |
| 5,961,370 A | 10/1999 | Valle et al. |
| 5,962,383 A | 10/1999 | Doyel et al. |
| 5,993,407 A * | 11/1999 | Moazed ............... A61F 9/00772 604/8 |
| 6,010,391 A | 1/2000 | Lewellen et al. |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson et al. |
| 6,149,684 A | 11/2000 | Herrick |
| 6,196,993 B1 | 3/2001 | Cohan et al. |
| 6,234,175 B1 | 5/2001 | Zhou et al. |
| 6,238,363 B1 * | 5/2001 | Kurihashi ............ A61F 9/00772 606/198 |
| 6,254,562 B1 | 7/2001 | Fouere |
| 6,264,971 B1 | 7/2001 | Darougar et al. |
| 6,290,684 B1 | 9/2001 | Herrick |
| 6,306,114 B1 | 10/2001 | Freeman et al. |
| 6,331,313 B1 | 12/2001 | Wong et al. |
| 6,344,047 B1 | 2/2002 | Price et al. |
| 6,371,122 B1 | 4/2002 | Mandelkorn |
| 6,375,972 B1 | 4/2002 | Guo et al. |
| 6,383,192 B1 | 5/2002 | Kurihashi |
| 6,428,502 B1 | 8/2002 | Lang |
| 6,455,062 B1 | 9/2002 | Olejnik et al. |
| 6,605,108 B2 | 8/2003 | Mendius et al. |
| 6,629,533 B1 | 10/2003 | Webb et al. |
| 6,706,275 B1 | 3/2004 | Camp |
| 6,729,939 B2 | 5/2004 | Wrue |
| 6,756,049 B2 | 6/2004 | Brubaker et al. |
| 6,780,164 B2 | 8/2004 | Bergheim et al. |
| 6,840,931 B2 | 1/2005 | Peterson et al. |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker et al. |
| 6,994,684 B2 | 2/2006 | Murray et al. |
| 7,017,580 B2 | 3/2006 | Prescott et al. |
| 7,117,870 B2 | 10/2006 | Prescott |
| 7,135,009 B2 | 11/2006 | Tu et al. |
| 7,204,253 B2 | 4/2007 | Mendius et al. |
| 7,204,995 B2 | 4/2007 | El-Sherif et al. |
| 8,333,726 B2 * | 12/2012 | Rapacki ............... A61F 9/00772 604/9 |
| 8,702,643 B2 * | 4/2014 | Rapacki ............... A61F 9/0017 604/9 |
| 9,445,944 B2 * | 9/2016 | Rapacki ............... A61F 9/0017 |
| 9,763,824 B2 * | 9/2017 | Rapacki ............... A61F 9/0017 |
| 10,434,009 B2 * | 10/2019 | Rapacki ............... A61F 9/0017 |
| 2002/0032400 A1 | 3/2002 | Moazed |
| 2002/0151960 A1 | 10/2002 | Mendius et al. |
| 2002/0198453 A1 | 12/2002 | Herrick |
| 2003/0130612 A1 | 7/2003 | Moazed |
| 2004/0102729 A1 | 5/2004 | Haffner et al. |
| 2004/0121014 A1 | 6/2004 | Guo et al. |
| 2004/0127843 A1 | 7/2004 | Tu et al. |
| 2004/0141151 A1 | 7/2004 | Gillespie |
| 2004/0147870 A1 | 7/2004 | Burns et al. |
| 2004/0175410 A1 | 9/2004 | Ashton et al. |
| 2004/0236343 A1 | 11/2004 | Taylor et al. |
| 2004/0249333 A1 | 12/2004 | Bergheim et al. |
| 2004/0265356 A1 | 12/2004 | Mosack |
| 2005/0095269 A1 | 5/2005 | Ainpour et al. |
| 2005/0192527 A1 | 9/2005 | Gharib et al. |
| 2005/0197614 A1 | 9/2005 | Pritchard et al. |
| 2005/0220882 A1 | 10/2005 | Pritchard et al. |
| 2005/0232972 A1 | 10/2005 | Odrich |
| 2005/0244469 A1 | 11/2005 | Whitcup et al. |
| 2005/0266047 A1 | 12/2005 | Tu et al. |
| 2005/0271704 A1 | 12/2005 | Tu et al. |
| 2005/0283109 A1 | 12/2005 | Peyman |
| 2006/0013835 A1 | 1/2006 | Anderson et al. |
| 2006/0020248 A1 | 1/2006 | Prescott |
| 2006/0020253 A1 * | 1/2006 | Prescott ............... A61F 9/00772 604/500 |
| 2006/0074370 A1 | 4/2006 | Zhou |
| 2006/0106352 A1 | 5/2006 | Kurihashi |
| 2006/0122553 A1 | 6/2006 | Hanna |
| 2007/0083146 A1 | 4/2007 | Murray |
| 2007/0092570 A1 | 4/2007 | Missel et al. |
| 2007/0123924 A1 | 5/2007 | Becker |
| 2007/0132125 A1 | 6/2007 | Rastogi et al. |
| 2007/0135914 A1 | 6/2007 | Herrick |
| 2007/0243230 A1 | 10/2007 | Juan et al. |
| 2007/0269487 A1 | 11/2007 | Juan et al. |
| 2007/0298075 A1 * | 12/2007 | Borgia ............... A61M 31/002 424/428 |
| 2007/0299515 A1 | 12/2007 | Herrick |
| 2007/0299516 A1 | 12/2007 | Cui et al. |
| 2008/0038317 A1 | 2/2008 | Chang et al. |
| 2008/0045878 A1 | 2/2008 | Bergheim et al. |
| 2008/0045911 A1 | 2/2008 | Borgia et al. |
| 2008/0181930 A1 | 7/2008 | Rodstrom et al. |
| 2009/0104243 A1 | 4/2009 | Utkhede et al. |
| 2009/0104248 A1 | 4/2009 | Rapacki et al. |
| 2009/0105749 A1 | 4/2009 | Juan et al. |

(56) References Cited

U.S. PATENT DOCUMENTS

| | | |
|---|---|---|
| 2009/0280158 A1 | 11/2009 | Butuner |
| 2009/0298390 A1 | 12/2009 | Rapacki et al. |
| 2010/0209477 A1 | 8/2010 | Butuner et al. |

FOREIGN PATENT DOCUMENTS

| | | |
|---|---|---|
| JP | 10033584 | 2/1998 |
| JP | 2004202276 A | 7/2004 |
| JP | 2005000628 A | 1/2005 |
| JP | 2005058622 A | 3/2005 |
| JP | 2005110765 A | 4/2005 |
| JP | 2005110930 A | 4/2005 |
| JP | 2005312835 A | 11/2005 |
| JP | 2005319190 A | 11/2005 |
| JP | 2005328922 A | 12/2005 |
| JP | 2007195819 A | 8/2007 |
| WO | 9833461 A1 | 8/1998 |
| WO | 9842282 A1 | 10/1998 |
| WO | 9937260 A1 | 7/1999 |
| WO | 9944553 A1 | 9/1999 |
| WO | 9964089 A1 | 12/1999 |
| WO | 9965544 A1 | 12/1999 |
| WO | 0027321 A1 | 5/2000 |
| WO | 0062760 A1 | 10/2000 |
| WO | 0211783 A1 | 2/2002 |
| WO | 02058667 A2 | 8/2002 |
| WO | 02083198 A2 | 10/2002 |
| WO | 03017897 A2 | 3/2003 |
| WO | 03022242 A1 | 3/2003 |
| WO | 03057101 A1 | 7/2003 |
| WO | 2004004614 A2 | 1/2004 |
| WO | 2004024043 A2 | 3/2004 |
| WO | 2004105658 A1 | 12/2004 |
| WO | 2004112639 A2 | 12/2004 |
| WO | 2005000154 A2 | 1/2005 |
| WO | 2005086694 A2 | 9/2005 |
| WO | 2006014434 A2 | 2/2006 |
| WO | 2006031658 A2 | 3/2006 |
| WO | 2006044669 A2 | 4/2006 |
| WO | 2006057859 A1 | 6/2006 |
| WO | 2006096586 A1 | 9/2006 |
| WO | 2007008262 A2 | 1/2007 |
| WO | 2007115259 A2 | 10/2007 |
| WO | 2007115261 A2 | 10/2007 |
| WO | 2007149771 A2 | 12/2007 |
| WO | 2007149832 A2 | 12/2007 |
| WO | 2008056060 A2 | 5/2008 |
| WO | 2009032328 A1 | 3/2009 |
| WO | 2010096822 A2 | 8/2010 |
| WO | 2010096822 A3 | 2/2011 |

OTHER PUBLICATIONS

"International Application Serial No. PCT/US2008/010487, International Search Report dated May 25, 2009", 5 pgs.

"International Application Serial No. PCT/US2008/010487, Written Opinion dated May 25, 2009", 8 pgs.

"International Application Serial No. PCT/US2008/010497, International Search Report dated Mar. 6, 2009".

"International Application Serial No. PCT/US2008/010497, Written Opinion dated Mar. 6, 2009".

"International Application Serial No. PCT/US2008/010502, International Search Report dated Mar. 5, 2009".

"International Application Serial No. PCT/US2008/010502, Written Opinion dated Mar. 5, 2009".

"International Application Serial No. PCT/US2010/025089, International Preliminary Report on Patentability dated Sep. 1, 2011".

"International Application Serial No. PCT/US2010/025089, International Search Report dated Dec. 10, 2010".

"International Application Serial No. PCT/US2010/025089, Written Opinion dated Dec. 10, 2010".

Examination Report as issued for European Patent Application No. 08830451.4, dated Nov. 5, 2010.

International Application Serial No. PCT/US2008/010479, International Search Report dated Dec. 15, 2008, 6 pgs.

International Application Serial No. PCT/US2008/010479, Written Opinion dated Dec. 15, 2008, 7 pgs.

Official Action as issued for Russian Patent Application No. 2010112426, dated Jun. 7, 2012.

\* cited by examiner

SECTION 3B-3B

SECTION 6B-6B

SECTION 8B-8B

SECTION 10B-10B

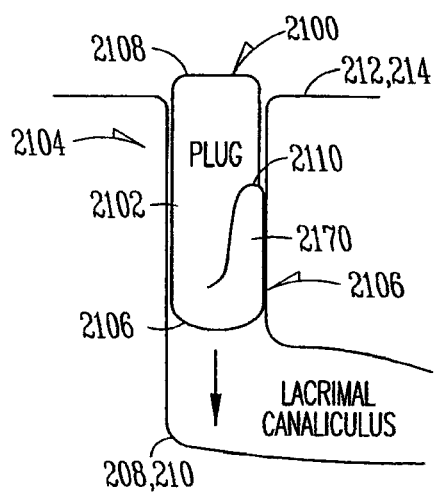
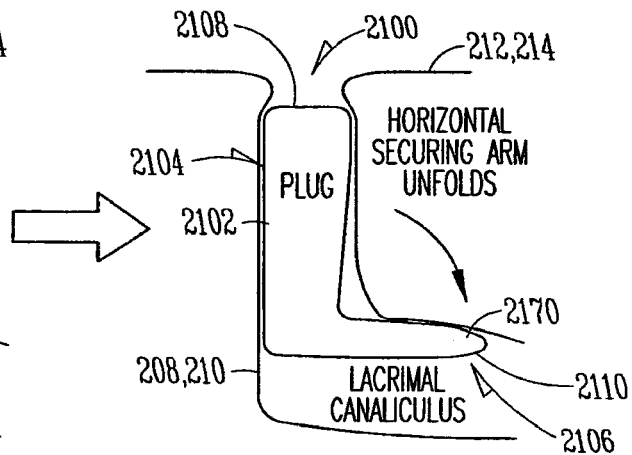
*FIG. 21A*  *FIG. 21B*
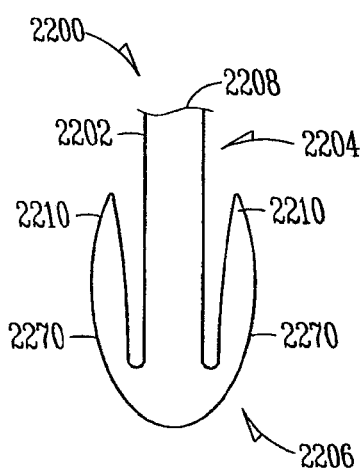
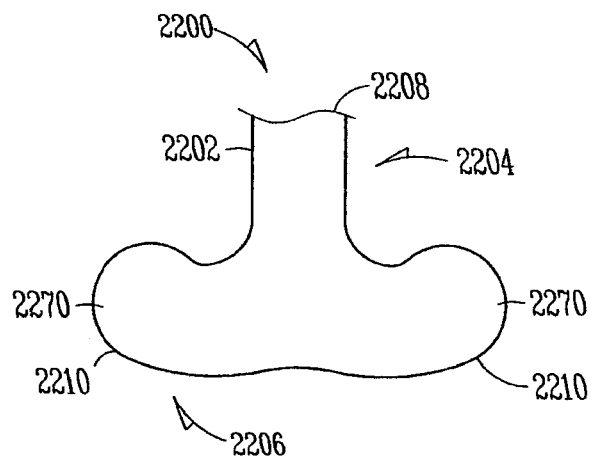
*FIG. 22A*  *FIG. 22B*

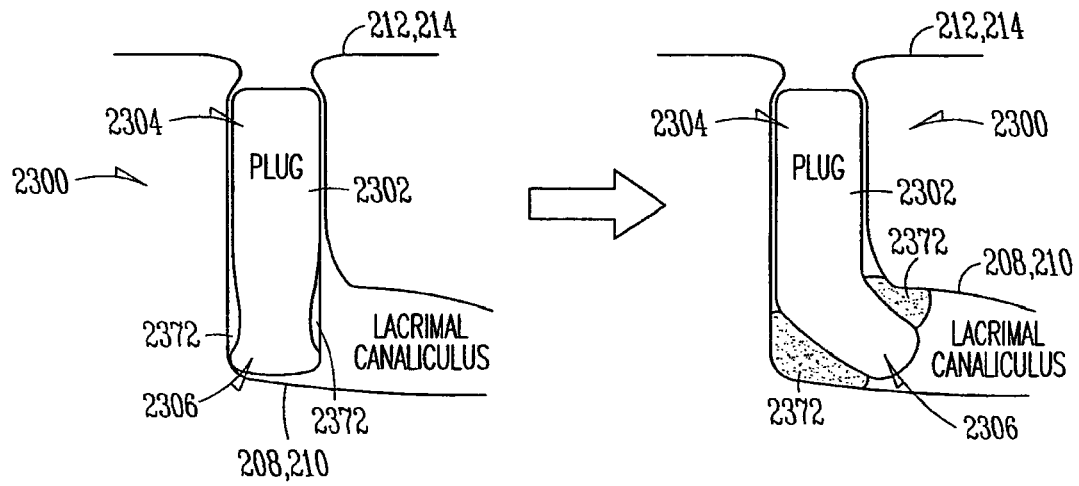
*FIG. 23A*  *FIG. 23B*
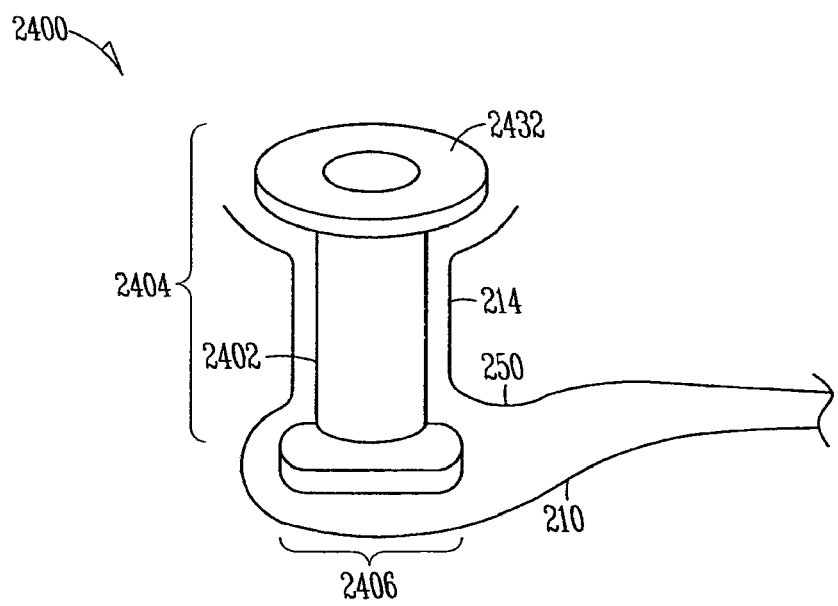
*FIG. 24*

LACRIMAL IMPLANTS AND RELATED METHODS

CLAIM OF PRIORITY

This application is a Continuation application of U.S. Ser. No. 15/707,386, filed 19 Sep. 2017, which is a Continuation application of U.S. Ser. No. 15/247,703, filed 25 Aug. 2016 (U.S. Pat. No. 9,763,824); which is a Continuation application of U.S. Ser. No. 14/192,915, filed 28 Feb. 2014 (U.S. Pat. No. 9,445,944); which is a Continuation application of U.S. Ser. No. 13/598,201, filed 29 Aug. 2012 (U.S. Pat. No. 8,702,643), which is a divisional application of U.S. Ser. No. 12/231,989 (U.S. Pat. No. 8,333,726), filed 8 Sep. 2008, which claims the benefit of priority under 35 U.S.C. § 119(e) to U.S. Provisional Patent Application Ser. No. 60/970,696 filed on 7 Sep. 2007; U.S. Provisional Patent Application Ser. No. 60/970,720 filed on 7 Sep. 2007; U.S. Provisional Patent Application Ser. No. 60/974,367 filed on 21 Sep. 2007; U.S. Provisional Patent Application Ser. No. 61/033,211 filed on 3 Mar. 2008; U.S. Provisional Patent Application Ser. No. 61/036,816 filed on 14 Mar. 2008; U.S. Provisional Patent Application Ser. No. 61/049,360 filed on 30 Apr. 2008; U.S. Provisional Patent Application Ser. No. 61/052,595 filed on 12 May 2008; and U.S. Provisional Patent Application Ser. No. 61/075,309 filed on 24 Jun. 2008, the specifications of all of which are herein incorporated by reference in their entireties.

TECHNICAL FIELD

This patent document pertains generally to ophthalmic devices, and particularly to ocular implants. More particularly, but not by way of limitation, this patent document pertains to lacrimal implants, methods of making such implants, and methods of treating ocular, respiration, inner ear or other diseases or disorders (e.g., pulmonary or immunological disorders) using such implants.

BACKGROUND

Dry eye, including keratoconjunctivitis sicca, is a common ocular condition that can require therapy. Dry eye has been experienced by a broad demographic band, and is common in elderly individuals. A variety of current treatment modalities target physiological conditions that contribute to dry eye, including augmentation of normal tear fluid, enhancement of tear film component production, and methods to enhance the residence time of tears, such as blocking the tear flow from an eye into and through a lacrimal canaliculus.

Many current tear flow blockage techniques have drawbacks, including being irreversible in nature. For instance, some tear flow blockage techniques involve closing the canalicular canal by stitching the punctal opening shut or by using electrical or laser cauterization to seal the punctal opening. Although such procedures can provide the desired result of blocking tear flow to treat a dry eye, they are unfortunately not reversible without reconstructive surgery.

In addition to dry eye symptom relief, a variety of challenges face patients and physicians in the area of ocular, respiration and inner ear disease or disorder management, including adequate drug or other therapeutic agent delivery to the eyes, nasal passage or inner ear. In ocular management, for example, many current ocular drug delivery systems require repetitive manual administration and are often ineffective due to a lack of patient compliance or inadequate drug concentrations reaching the eye.

In order to treat eye infection, inflammation of an eye, glaucoma and other ocular diseases or disorders, drugs or other therapeutic agents are often required to be administered to the eye. A conventional method of drug delivery is by topical drop application to the eye's surface. Topical eye drops, though effective, can be inefficient. As one example, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can absorbingly treat the eye. Moreover, topically applied drugs often have a peak ocular effect for about two hours post-application, after which additional applications of the drugs should be, but are often not, administered to maintain the desired drug therapeutic benefit.

To compound ocular management difficulty, patients often do not use their eye drops as prescribed. This poor compliance can be due to, for example, an initial stinging or burning sensation caused by the eye drop and experience by a patient. Instilling eye drops in one's own eye can be difficult, in part because of the normal reflex to protect the eye. Therefore, one or more drops may miss the eye. Older patients may have additional problems instilling drops due to arthritis, unsteadiness, and decreased vision. Pediatric and psychiatric populations pose difficulties as well.

In a field different from ocular management, control of respiration-related (e.g., allergies) and inner ear diseases or disorders often requires repetitive manual digestion or other intake of a medication (e.g., drugs or other therapeutic agents), and as such, can be ineffective due to a lack of patient compliance or non-localized drug delivery.

EXEMPLARY ASPECTS AND EMBODIMENTS OF THE INVENTION

The present inventors have recognized various promising techniques to increase the residence time of tears on an eye and delivery of drug or other therapeutic agent to the eye, nasal passage, inner ear or other system. These techniques can include placing a removable, and optionally drug releasing, lacrimal implant through a lacrimal punctum and into the associated canaliculus. It is believed that by designing lacrimal implants that utilize the features of the nasolacrimal drainage system, patient comfort and implant retention in the ocular anatomy can be satisfied. In this way, the present lacrimal implants can overcome some of the drawbacks associated with current dry eye relief, such as being irreversible in nature, and ocular drug administration (e.g., manual drop instillation or digestion), such as poor patient compliance, waste, untimely application, or non-localized delivery.

Further yet, the present inventors have recognized that a lacrimal implant can benefit from one or more of: the ability to be easily implanted and removed without much biasing of the lacrimal punctum or associated canaliculus, the ability to be securely retainable in the lacrimal canaliculus upon implantation, optionally without being pre-sized to a particular lacrimal punctum or canaliculus, the ability to permit tear fluid, drug or other agent to flow into the nasolacrimal system, and, when made and used as a drug delivery system, the ability to allow for the sustained, localized release of one or more drugs or other therapeutic agents at a desired therapeutic level for an extended period of time.

Lacrimal implants for treating diseases or disorders are disclosed. More particularly, lacrimal implants, methods of making such implants, and methods of treating ocular, respiration, inner ear, pulmonary or immunological diseases or disorders using such implants are disclosed.

To better illustrate the subject matter described herein, a non-limiting list of exemplary aspects and embodiments is provided here:

1. A lacrimal implant insertable into a lacrimal canaliculus, comprising: an implant body, including first and second portions, the implant body extending from a proximal end of the first portion to a distal end of the second portion; the proximal end of the first portion defining a longitudinal proximal axis and the distal end of the second portion defining a longitudinal distal axis; the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature; and wherein the second portion of the implant body includes a longitudinal length having a magnitude less than four times a longitudinal length of the first portion of the implant body.

2. The lacrimal implant according to aspect 1, wherein the implant body is configured such that an angled intersection exists between the proximal axis and the distal axis prior to being implanted in the lacrimal canaliculus.

3. The lacrimal implant according to any of aspects 1 or 2, wherein the implant body is configured to partially or completely inhibit fluid flow into and through the lacrimal canaliculus.

4. The lacrimal implant according to any of aspects 1-3, wherein a distal end of the first portion is integral with the second portion at or near a proximal end of the second portion.

5. The lacrimal implant according to any of aspects 1-4, wherein one or both of the first portion or the second portion includes a fluid swellable retention element configured to expand.

6. The lacrimal implant according to aspect 5, wherein the second portion includes the fluid swellable retention element, the fluid swellable retention element configured to expand laterally, relative to the proximal axis of the first portion, when the implant body is implanted.

7. The lacrimal implant according to any of aspects 5 or 6, wherein the fluid swellable retention element includes a portion configured to expand laterally in a direction away from a lacrimal canaliculus ampulla when the implant body is implanted.

8. The lacrimal implant according to any of aspects 5-7, wherein the fluid swellable retention element includes a portion configured to expand laterally in a direction toward a lacrimal canaliculus ampulla when the implant body is implanted.

9. The lacrimal implant according to any of aspects 1-8, wherein the second portion includes an expandable retention element comprising at least one of a coil, a braid, a stent, a mesh tube, a suture, a thermoset polymer, a thermoplastic, a heat activatable material, or a shape memory material, the expandable retention element configured to expand laterally, to form the angled intersection, when the implant body is implanted.

10. The lacrimal implant according to any of aspects 1-9, comprising an expandable retention element disposed around a portion of the second portion, the expandable retention element configured to bias the second portion away from a wall of the lacrimal canaliculus upon expansion.

11. The lacrimal implant according to any of aspects 1-10, wherein the second portion includes an arm member movable between a first configuration and a second configuration; the arm member, in the first configuration, disposable along the implant body for insertion into the lacrimal canaliculus and, in the second configuration, laterally extendable from one side of the implant body.

12. The lacrimal implant according to any of aspects 1-11, wherein the second portion includes an integral dilator, the integral dilator generally narrowing from a location near a proximal end of the second portion to the distal end of the second portion to facilitate implantation of the implant body into the lacrimal canaliculus.

13. The lacrimal implant according to aspect 12, wherein a diameter of an integral dilator tip is between about 0.2 millimeters and about 0.5 millimeters.

14. The lacrimal implant according to any of aspects 12 or 13, wherein an outer surface slope of the integral dilator, as measured from the location near the proximal end of the second portion to the distal end of the second portion, is between about 1 degree and about 10 degrees with respect to the distal axis.

15. The lacrimal implant according to any of aspects 1-14, wherein the second portion includes at least one undulation.

16. The lacrimal implant according to any of aspects 1-15, wherein at least one of the first portion or the second portion comprises at least one intermediately-disposed annular, semi-annular, column-like, or barrel-like projection, the intermediately-disposed projection having a cross-sectional size greater than an adjacent implant body portion.

17. The lacrimal implant according to any of aspects 1-16, comprising a graspable projection extending at least partially from the proximal end of the first portion, the graspable projection configured to seat against or near a lacrimal punctum when the implant body is implanted.

18. The lacrimal implant according to aspect 17, wherein the second portion includes an element extending or expanding laterally into a lacrimal canaliculus ampulla when the implant body is implanted.

19. The lacrimal implant according to any of aspects 17 or 18, wherein the graspable projection extends laterally from the proximal end of the first portion, in a direction that is parallel to or away from an eye, when the implant body is implanted.

20. The lacrimal implant according to any of aspects 1-19, wherein the implanted angled intersection of the proximal axis and the distal axis is at least about 45 degrees.

21. The lacrimal implant according to any of aspects 1-20, comprising a therapeutic agent.

22. The lacrimal implant according to aspect 21, comprising at least one drug insert including a drug core, the drug core comprising the therapeutic agent.

23. The lacrimal implant according to aspect 22, wherein the drug core comprises at least one exposed surface to deliver a sustained release.

24. A kit comprising the lacrimal implant according to any of aspects 1-23, and an instruction for using the lacrimal implant to treat an eye disease.

25. A kit comprising the lacrimal implant according to any of aspects 1-23, and an instruction for using the lacrimal implant to treat a respiration-related disorder.

26. A kit comprising the lacrimal implant according to any of aspects 1-23, and an instruction for using the lacrimal implant to treat an inner ear disorder.

27. A lacrimal implant for insertion into a lacrimal canaliculus, comprising: an implant body non-linearly extending from a proximal end portion positionable within a vertical section of the lacrimal canaliculus to a distal end portion positionable within a horizontal section of the lacrimal canaliculus and having an intermediate portion therebetween; the intermediate portion partially extending in a first direction toward the proximal end portion and partially extending in a second direction toward the distal end portion such that, when implanted in the lacrimal canaliculus, the implant body directionally biases laterally against at least a portion of the lacrimal canaliculus located at or more distal to a canalicular curvature; and wherein the implant body inhibits fluid flow into and through the lacrimal canaliculus.

28. The lacrimal implant according to aspect 27, wherein a longitudinal length of the implant body positionable within the vertical section of the lacrimal canaliculus is less than four times a longitudinal length of the implant body positionable within the horizontal section of the lacrimal canaliculus.

29. The lacrimal implant according to any of aspects 27 or 28, wherein the first direction extension of the intermediate portion is at an angle between about 45 degrees and about 135 degrees relative to the second direction extension of the intermediate portion.

30. The lacrimal implant according to any of aspects 27-29, wherein the intermediate portion partially extends in a third direction, substantially opposite the second direction, toward a lacrimal canaliculus ampulla when the implant body is implanted.

31. The lacrimal implant according to any of aspects 27-30, wherein the second direction extension includes a longitudinal dilator having a generally concave shape relative to the first direction extension; and wherein a radius of the generally concave shape is less than the radius of the canaliculus curvature.

32. The lacrimal implant according to any of aspects 27-31, wherein the second direction extension includes a longitudinal dilator having a generally convex shape relative to the first direction extension.

33. The lacrimal implant according to any of aspects 27-32, wherein the second direction extension includes a longitudinal dilator having an axis substantially perpendicular to an axis of the first direction extension.

34. The lacrimal implant according to any of aspects 27-33, wherein at least one of the proximal end portion or the distal end portion comprises at least one intermediately-disposed annular, semi-annular, column-like, or barrel-like projection, the intermediately-disposed projection having a cross-sectional size greater than an adjacent implant body portion.

35. The lacrimal implant according to any of aspects 27-34, comprising a graspable projection, the graspable projection extending laterally from the proximal end portion.

36. The lacrimal implant according to any of aspects 27-35, comprising a fluid swellable material disposed on an outer surface portion of the implant body, the fluid swellable material configured to expand an outer surface diameter portion of the implant body when implanted.

37. The lacrimal implant according to any of aspects 27-36, comprising at least one of a first drug insert disposed in the proximal end portion or a second drug insert disposed in the distal end portion, one or both of the first or second drug inserts inhibiting fluid flow through the implant body and including at least one exposed surface configured to deliver a sustained release.

38. The lacrimal implant according to aspect 37, comprising a cavity in the proximal end portion, the cavity configured to house the first drug insert in the form of a drug core, the drug core including a first agent configured to treat an eye.

39. The lacrimal implant according to any of aspects 37 or 38, comprising a cavity in the distal end portion, the cavity configured to house the second drug insert in the form of a drug core, the drug core including a second agent configured to be received by a nasal passage.

40. A method of manufacturing a lacrimal implant insertable into a lacrimal canaliculus, the method comprising: forming an implant body extending from a proximal end of a first body portion to a distal end of a second body portion, including extending the second body portion to a longitudinal length which is less than four times a longitudinal length of the first body portion; and configuring the proximal end and the distal end to respectively define, when implanted in the lacrimal canaliculus, a longitudinal proximal axis and a longitudinal distal axis that intersect at an angle such that the implant body is configured to directionally bias laterally against at least a portion of the lacrimal canaliculus located at or more distal to a canaliculus curvature.

41. The method according to aspect 40, wherein forming one or both of the first body portion or the second body portion includes forming at least one intermediately-disposed annular, semi-annular, column-like, or barrel-like projection, the intermediately-disposed projection having a cross-sectional size greater than an adjacent implant body portion.

42. The method according to any of aspects 40 or 41, wherein forming the second body portion includes forming a dilator generally narrowing from a location near a proximal end of the second body portion to the distal end of the second body portion.

43. The method according to any of aspects 40-42, wherein forming the dilator includes forming an outer surface slope of the implant body, as measured from the location near the proximal end of the second body portion to the distal end of the second body portion, between about 1 degree and about 10 degrees with respect to the longitudinal distal axis.

44. The method according to any of aspects 40-43, wherein forming the second potion includes disposing a fluid swellable retention element near a distal end of the first body portion, including disposing the fluid swellable retention element such that a lateral expansion thereof, relative to the proximal axis, is configured to bias against at least a portion of the lacrimal canaliculus or a lacrimal canaliculus ampulla anatomy when the implant body is implanted.

45. The method according to any of aspects 40-44, comprising coating an outer surface portion of the implant body with a fluid swellable material.

46. The method according to any of aspects 40-45, comprising disposing at least one of a first drug insert in the first body portion or a second drug insert in the second body portion, including positioning at least one of an exposed surface of the first drug insert adjacent to the proximal end or an exposed surface of the second drug insert adjacent to the distal end to provide a sustained release of a first agent or a second agent, respectively.

47. A method of treating a patient having at least one of an eye disorder, a respiration-related disorder, a pulmonary disorder, an immunological disorder or an inner ear disorder, the method comprising: inserting a lacrimal implant into at least one lacrimal canaliculus of the patient, the lacrimal implant comprising, an implant body, including first and second portions, the implant body extending from a proximal end of the first portion to a distal end of the second portion, the proximal end defining a longitudinal proximal axis and the distal axis defining a longitudinal distal axis; the implant body configured such that, when implanted in a lacrimal canaliculus, an angled intersection exists between the proximal axis and the distal axis for biasing at least a portion of the implant body against at least a portion of the lacrimal canaliculus located at or more distal to a canalicular curvature; and at least one of a first drug insert disposed in the first portion or a second drug insert disposed in the second portion, the first and second drug inserts configured to respectively provide a sustained release of a first agent or a second agent.

48. The method according to aspect 47, wherein inserting the lacrimal implant includes concurrently dilating the lacrimal canaliculus, using an integral dilator of the implant body, as the distal end of the second portion is moved into the lacrimal canaliculus.

49. The method according to any of aspects 47 or 48, comprising removing the inserted implant body from the lacrimal canaliculus.

50. The method according to any of aspects 47-49, comprising replacing the lacrimal implant that has been inserted with a second lacrimal implant including at least one of the same first or second agent following an interval of time.

These and other embodiments, advantages, and aspects of the present lacrimal implants and methods will be set forth in part in following Detailed Description. This Summary is intended to provide an overview of subject matter of the present patent application. It is not intended to provide an exclusive or exhaustive explanation of the present invention. The Detailed Description is included to provide further information about the present patent application.

BRIEF DESCRIPTION OF THE DRAWINGS

In the drawings, like numerals can be used to describe similar components throughout the several views. Like numerals having different letter suffixes can be used to represent different instances of similar components. The drawings illustrate generally, by way of example, but not by way of limitation, various embodiments discussed in the present document.

FIGS. 21A-22B illustrate examples of a side view of lacrimal implants configured to be retained within a lacrimal punctum and associated canalicular anatomy, each lacrimal implant including one or more laterally extendable arms.

FIGS. 23A-23B illustrate examples of a side view of a lacrimal implant configured to be retained within a lacrimal punctum and associated canalicular anatomy, the lacrimal implant including an expandable retention element disposed around a portion of the implant body.

FIG. 24 illustrates an example of a schematic view of a lacrimal implant retained within a lacrimal punctum and associated canalicular anatomy.

DETAILED DESCRIPTION

In this patent document, lacrimal implants and related methods providing secure, wedgable retention within a lacrimal punctum and associated canaliculus of an eye are described. The lacrimal implants can comprise an implant body configured for at least partial insertion through the lacrimal punctum and into the associated canaliculus. The implant body can include first and second portions, and can extend from a proximal end of the first portion defining a longitudinal proximal axis to a distal end of the second portion defining a longitudinal distal axis. The implant body can be configured such that, when implanted using an integral dilator, an at least 45 degree angled intersection, for example, exists between the proximal axis and the distal axis. In this way, at least a portion of the implant body can be biased against at least a portion of the lacrimal canaliculus located at or more distal to a canalicular curvature, thereby retaining an implanted position of the lacrimal implant using anatomical structures. In various examples, the lacrimal implant can further comprise a drug insert including a drug insert disposed in at least one of the first portion or the second portion of the implant body, providing a sustained release of a drug or other therapeutic agent to one or more of an eye, nasal passage or inner ear system.

Figure 1:
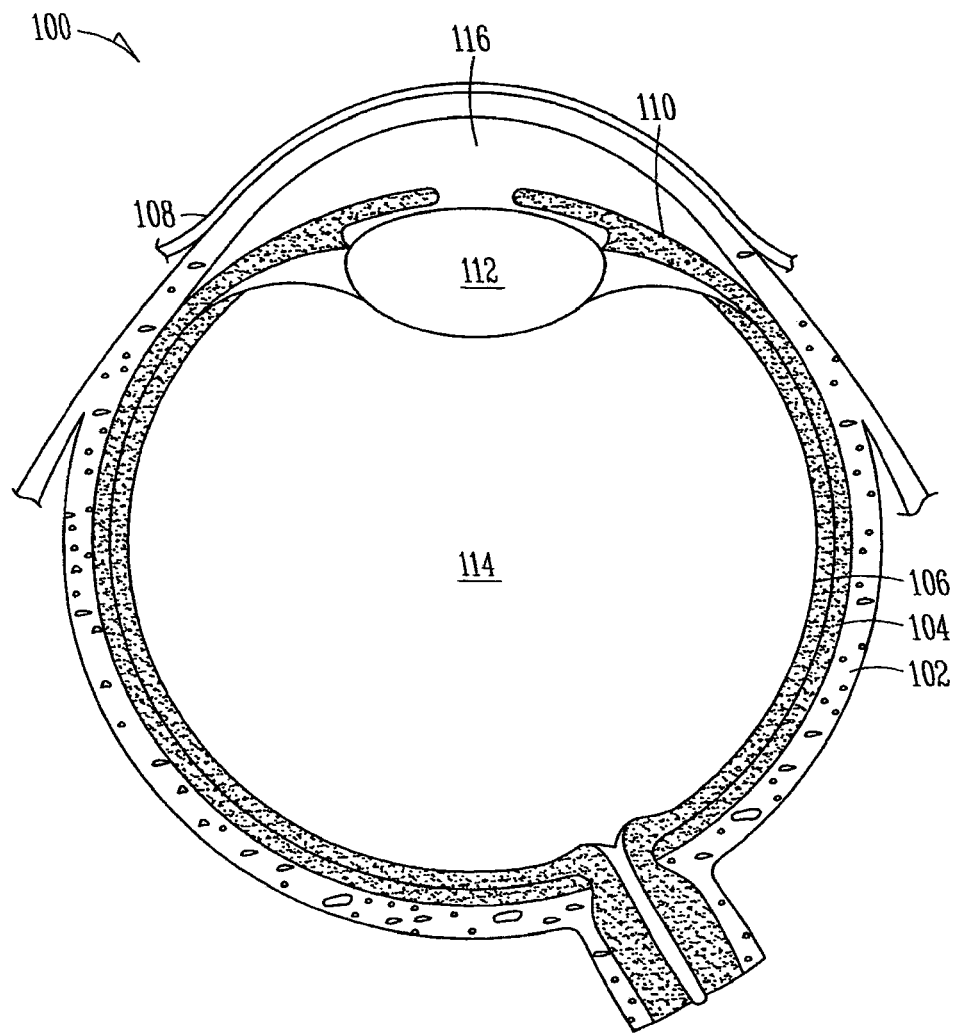
FIGS. 1-2 illustrate examples of schematic views of anatomical tissue structures associated with the eye, such tissue structures providing a suitable environment in which a lacrimal implant can be used.
Figure 2:
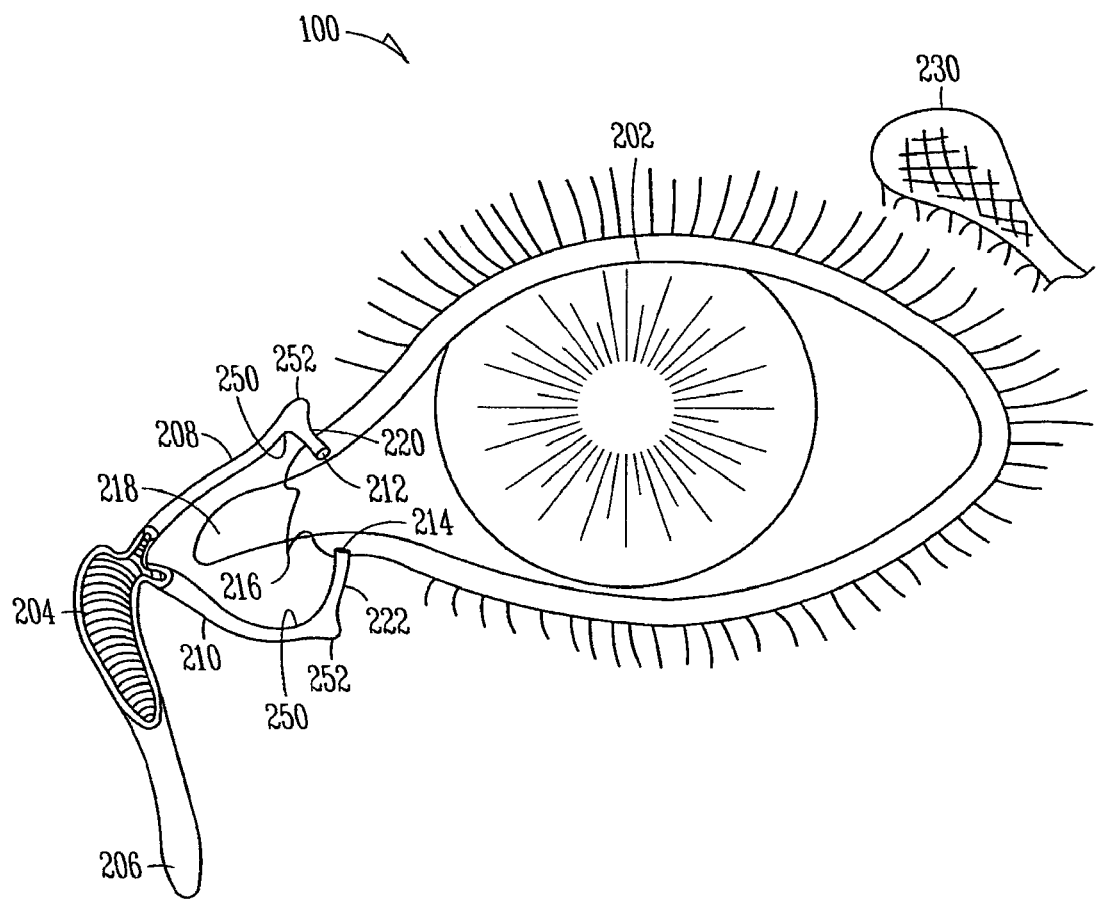

FIGS. 1-2 illustrate examples of schematic views of anatomical tissue structures associated with an eye 100. The anatomical tissue structures shown are suitable for treatment using the various lacrimal implants and methods discussed herein. As shown, the eye 100 is a spherical structure including a wall having three layers: an outer sclera 102, a middle choroid layer 104 and an inner retina 106. The sclera 102 includes a tough fibrous coating that protects the inner layers. It is mostly white except for the transparent area at the front, commonly known as the cornea 108, which allows light to enter the eye 100.

The choroid layer 104, situated inside the sclera 102, contains many blood vessels and is modified at the front of the eye 100 as a pigmented iris 110. A biconvex lens 112 is situated just behind the pupil. A chamber 114 behind the lens 112 is filled with vitreous humour, a gelatinous substance. Anterior and posterior chambers 116 are situated between the cornea 108 and iris 110, respectively and filled with aqueous humour. At the back of the eye 100 is the light-detecting retina 106.

The cornea 108 is an optically transparent tissue that conveys images to the back of the eye 100. It includes avascular tissue to which nutrients and oxygen are supplied via bathing with lacrimal fluid and aqueous humour as well as from blood vessels that line the junction between the cornea 108 and sclera 102. The cornea 108 includes a pathway for the permeation of drugs into the eye 100.

Turning to FIG. 2, other anatomical tissue structures associated with the eye 100 including the lacrimal drainage system, which includes a secretory system 230, a distributive system and an excretory system, are shown. The secretory system 230 comprises secretors that are stimulated by blinking and temperature change due to tear evaporation and reflex secretors that have an efferent parasympathetic nerve supply and secrete tears in response to physical or emotional stimulation. The distributive system includes the eyelids 202 and the tear meniscus around the lid edges of an open eye, which spread tears over the ocular surface by blinking, thus reducing dry areas from developing.

The excretory part of the lacrimal drainage system includes, in order of flow drainage, the lacrimal puncta, the lacrimal canaliculi, the lacrimal sac 204 and the lacrimal duct 206. From the lacrimal duct 206, tears and other flowable materials drain into a passage of the nasolacrimal system. The lacrimal canaliculi include an upper (superior) lacrimal canaliculus 208 and a lower (inferior) lacrimal canaliculus 210, which respectively terminate in an upper 212 and lower 214 lacrimal punctum. The upper 212 and lower 214 punctum are slightly elevated at the medial end of a lid margin at the junction 216 of the ciliary and lacrimal portions near a conjunctival sac 218. The upper 212 and lower 214 punctum are generally round or slightly ovoid openings surrounded by a connective ring of tissue. Each of puncta 212, 214 leads into a vertical portion 220, 222 of their respective canaliculus before turning more horizontal at a canaliculus curvature 250 to join one another at the entrance of the lacrimal sac 204. The canaliculi 208, 210 are generally tubular in shape and lined by stratified squamous epithelium surrounded by elastic tissue, which permits them to be dilated. As shown, a lacrimal canaliculus ampulla 252 exists near an outer edge of each canaliculus curvature 250.

Figure 3A:
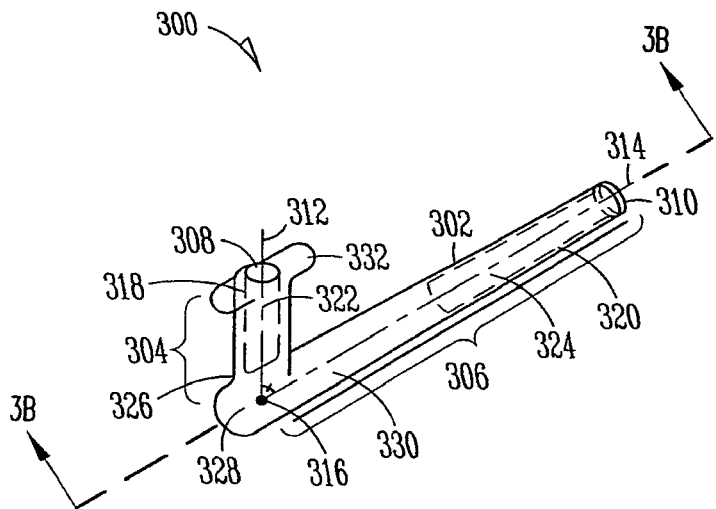
FIG. 3A illustrates an example of an isometric view of a lacrimal implant configured to be retained within a lacrimal punctum and associated canalicular anatomy, the lacrimal implant including a substantially perpendicular angled intersection between first and second implant body portions.

FIG. 3A illustrates an example of a lacrimal implant 300 that can be insertable through a lacrimal punctum 212, 214 and into the associated canaliculus 208, 210 (FIG. 2). The insertion of the lacrimal implant 300 through the lacrimal punctum 212, 214 and into the associated canaliculus 208, 210 can allow for one or more of: inhibition or blockage of tear flow therethrough (e.g., to treat dry eyes) or the sustained delivery of a drug or other therapeutic agent to an eye (e.g., to treat an infection, inflammation, glaucoma or other ocular disease or disorder), a nasal passage (e.g., to treat a sinus or allergy disorder) or an inner ear system (e.g., to treat dizziness or a migraine).

As shown in this example, the lacrimal implant 300 can comprise an implant body 302 including first 304 and second 306 portions, and can extend from a proximal end 308 of the first portion 304 to a distal end 310 of the second portion 306. In various examples, the proximal end 308 can define a longitudinal proximal axis 312 and the distal end 310 can define a longitudinal distal axis 314. The implant body 300 can be configured such that, when implanted within the lacrimal punctum and associated canaliculus, an at least 45 degree angled intersection 316 exists between the proximal axis 312 and the distal axis 314 for biasing at least a portion of the implant body 302 against at least a portion of a lacrimal canaliculus 208, 210 (FIG. 2) located at or more distal to a canaliculus curvature 250 (FIG. 2). In some examples, the implant body 302 can be configured such that the angled intersection 316 is between about 45 degrees and about 135 degrees. In this example, the implant body 302 is configured such that the angled intersection 316 is about 90 degrees (i.e., the intersection 316 is about perpendicular). In various examples, a distal end 326 of the first portion 304 can be integral with the second portion 306 at or near a proximal end 328 of the second portion 306.

In certain examples, the implant body 302 can include angularly disposed cylindrical-like structures comprising one or both of a first cavity 318 disposed near the proximal end 308 or a second cavity 320 disposed near the distal end 310. In this example, the first cavity 318 extends inward from the proximal end 308 of the first portion 304, and the second cavity 320 extends inward from the distal end 310 of the second portion 306. A first drug-releasing or other agent-releasing insert (e.g., drug core) 322 can be disposed in the first cavity 318 to provide a sustained drug or other therapeutic agent release to an eye, while a second drug-releasing or other agent-releasing insert (e.g., drug core) 324 can be disposed in the second cavity 320 to provide a sustained drug or other therapeutic agent release to a nasal passage or inner ear system, for example. An implant body septum 330 can be positioned between the first cavity 318 and the second cavity 320, and can be used to inhibit or prevent communication of a material (e.g., agent) between the first drug insert 322 and the second drug insert 324. In some examples, the implant body 302 is solid and does not include one or more cavities or other voids.

In some examples, the drug or other therapeutic agent release can occur, at least in part, via an exposed, non-sheath covered, surface of the drug inserts 322, 324. In some examples, by controlling geometry of the exposed surface, a predetermined drug or agent release rate can be achieved. For instance, the exposed surface can be constructed with a specific geometry or other technique appropriate to control the release rate of the drug or other therapeutic agent onto an eye 100, such as on an acute basis or on a chronic basis, between outpatient doctor visits. Further description regarding effective release rates of one or more drugs or other therapeutic agents from a drug insert 322, 324 can be found in commonly-owned DeJuan et al., U.S. patent application Ser. No. 11/695,545, filed on Apr. 2, 2007 entitled "NASOLACRIMAL DRAINAGE SYSTEM IMPLANTS FOR DRUG THERAPY," issued as U.S. Pat. No. 7,998,497 on Aug. 16, 2011, and which is herein incorporated by reference in its entirety, including its description of obtaining particular release rates.

Figure 3B:
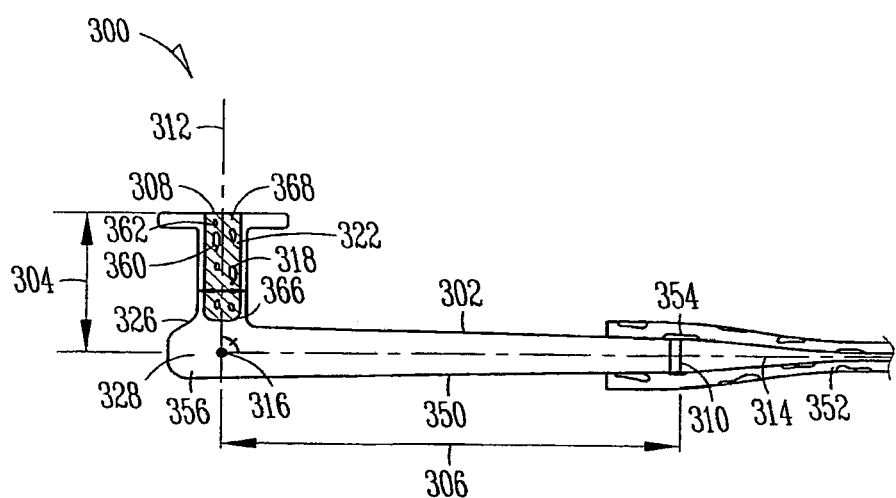
FIG. 3B illustrates an example of a cross-sectional view of a lacrimal implant taken along a line parallel to a longitudinal axis of the implant, such as along line 3B-3B, and a dilation of an implant-receiving anatomical tissue structure.
Figure 4:
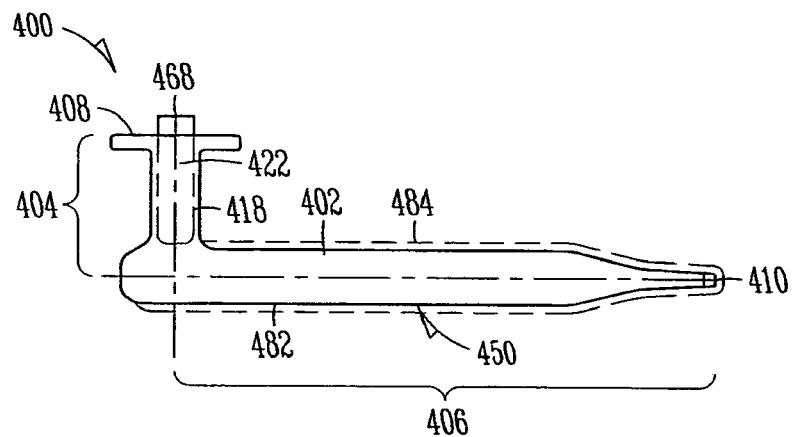
FIG. 4 illustrates an example of a side view of a lacrimal implant configured to be retained within a lacrimal punctum and associated canalicular anatomy, the lacrimal implant including an integral dilator.

In some examples, such as is shown in FIG. 3B, the exposed surface of the drug insert 322, 324 can be flush or slightly below the proximal end 308 of the first portion 304 or the distal end 310 of the second portion 306, respectively, such that the drug insert does not protrude outside of the implant body 302. In some examples, such as is shown in FIG. 4, the exposed surface of the first drug insert 322, for instance, can be positioned above the proximal end 308 such that the first drug insert 322 at least partially protrudes outside of the implant body 302.

The implant body 302 can include a graspable or other projection 332, such as one or more projections extending laterally at least partially from or around a proximal end 308 of the first implant body portion 304. In some examples, the graspable or other projection 332 can include a set of wings for use in inserting the lacrimal implant 300 into, or removing the lacrimal implant 300 from, an implanted position. The set of wings or other projection 332 can be configured without migration in mind, as the non-linear configuration of the implant body 302 can prevent implant 300 migration by assuming a size or shape of the canaliculus curvature 250 and optionally, the lacrimal canaliculus ampulla 252 (FIG. 2). In some examples, the graspable or other projection 332 can be configured to seat against or near the punctal opening 212, 214, such as for inhibiting or preventing the lacrimal implant 300 from passing completely within the lacrimal canaliculus 208, 210, or for providing tactile or visual feedback information to an implanting user, e.g., as to whether the implant is fully implanted.

Figure 34A:
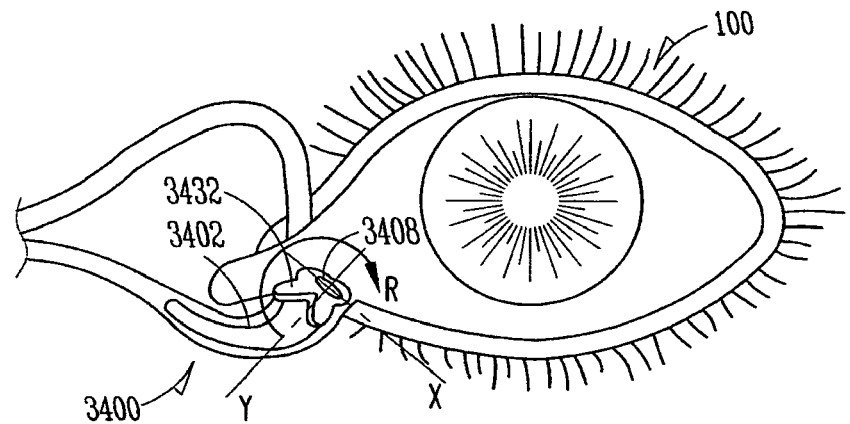
FIGS. 34A-34B illustrate examples of a schematic view of lacrimal implants retained within a lacrimal punctum and associated canalicular anatomy, each lacrimal implant including an oriented graspable projection.
Figure 34B:
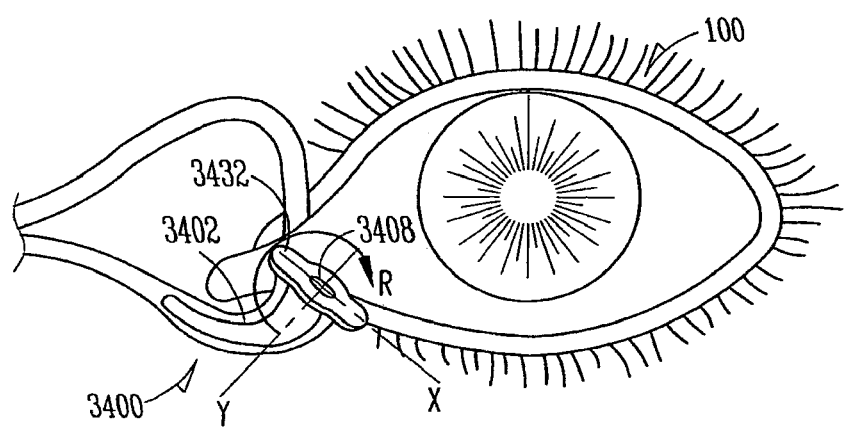

As shown in FIGS. 34A-34B, and discuss below, the graspable or other projection 332 can extend laterally in a direction parallel to or away from an eye 100 when implanted. This may reduce irritation to the eye 100 as compared to a case in which a portion of the projection extends toward the eye 100. In addition, a lateral extension direction of the projection 332 from the proximal end 308 can be substantially the same as a lateral extension direction of the second implant body portion 306 relative to the distal end 326 of the first implant body portion 304, as shown in FIGS. 3A-3B, for example. This can also avoid extension toward the eye. The first drug insert 322 can partially extend though the region of the projection 332, such as to provide sustained release of a first drug or other therapeutic agent onto an eye.

In various examples, the implant body 302 can be molded using an elastic material, such as silicone, polyurethane or other urethane-based polymer or copolymer, NuSil (e.g., NuSil 4840 with 2% 6-4800) or an acrylic of a non-biodegradable, partially biodegradable or biodegradable nature (i.e., erodeable within the body) allowing an implant body 302 configured such that, when implanted in a lacrimal canaliculus 208, 210, an angled intersection 316 exists between a proximal 312 and distal 314 axis to be formed. In some examples, the biodegradable elastic materials can include cross-linked polymers, such as poly (vinyl alcohol). In some examples, the implant body 302 can comprise a silicone/polyurethane co-polymer. Other co-polymers that can be used to form the implant body 302 include, but are not limited to, silicone/urethane, silicone/poly (ethylene glycol) (PEG), and silicone/2hydroxyethyl methacrylate (HEMA). As discussed in commonly-owned Utkhede et al., U.S. patent application Ser. No. 12/23,986, filed on Sep. 5, 2008, entitled "DRUG CORES FOR SUSTAINED RELEASE OF THERAPEUTIC AGENTS," published as U.S. Patent Application Publication No. 2009/0104243 on Apr. 23, 2009, and which is herein incorporated by reference in its entirety, urethane-based polymer and copolymer materials allow for a variety of processing methods and bond well to one another.

FIG. 3B illustrates an example of a cross-sectional view of the lacrimal implant 300 taken along a line parallel to a longitudinal axis of the implant, such as along line 3B-3B of FIG. 3A. As shown in FIG. 3B, the lacrimal implant 300 can include an implant body 302 including first 304 and second 306 portions, and can extend from a proximal end 308 of the first portion 304 to a distal end 310 of the second portion 306. In various examples, the proximal end 308 can define a longitudinal proximal axis 312 and the distal end 310 can define a longitudinal distal axis 314. The implant body 300 can be configured such that, when implanted, an at least 45 degree angled intersection 316 exists between the proximal axis 312 and the distal axis 314 for biasing at least a portion of the implant body 302 against at least a portion of a lacrimal canaliculus 208, 210 (FIG. 2) located at or more distal to a canaliculus curvature 250 (FIG. 2).

In this example, the implant body 300 is configured such that the angled intersection 316 is approximately about 90 degrees.

In various examples, a distal end 326 of the first portion 304 can be integral with the second portion 306 at or near a proximal end 328 of the second portion 306. In some examples, the second portion 306 can include a length having a magnitude less than four times a length of the first portion 304. In one example, the second portion 306 can include a length of less than about 10 millimeters and have a configured similar to that shown in FIG. 3B. In another example, the second portion 306 can include a length less than about 2 millimeters and have a configuration similar to that shown in FIG. 24.

In various examples, the second portion 306 can comprise an integral dilator 350 to dilate anatomical tissue 352, such as one or both of a lacrimal punctum 212, 214 (FIG. 2) or associated canaliculus 208, 210, to a sufficient diameter as the lacrimal implant 300 is being implanted. In this way, the lacrimal implant 300 can be implanted in various size ocular anatomies without the need for pre-dilation via a separate enlarging tool. The dilator 350 can be formed so as to not be traumatic to an inner lining of the punctum 212, 214 and the canaliculus 208, 210. In some examples, a lubricious coating disposed on, or impregnated in, an outer surface of the implant body 302 can be used to further aid insertion of the lacrimal implant 300 into the anatomical tissue 352. In one example, the lubricious coating can include a silicone lubricant.

As shown, the dilator 350 can generally narrow from a location near the proximal end 328 of the second portion 306 to the distal end 310 of the second portion 306, such as from a diameter of about 0.6 millimeters to a diameter of about 0.2 millimeters. In some examples, an outer surface slope of the dilator 350, as measured from the location near the proximal end 328 of the second portion 306 to the distal end 310 of the second portion 306, can be between about 1 degree and about 10 degrees (e.g., 2 degrees, 3 degrees, 4 degrees, or 5 degrees) with respect to the longitudinal distal axis 314. In some examples, the slope of the dilator 350 can be less than 45 degrees with respect to the longitudinal distal axis 314. Among other factors, a determination of a desirable dilator 350 slope for a given implant situation can be made by balancing an implant body 302 strength desirable for implantation with a desire to have a soft, flexible and conforming implant body (e.g., to conform to a lacrimal canaliculus anatomy) upon implantation. In some examples, a diameter of a dilator tip 354 can be between about 0.2 millimeters and about 0.5 millimeters.

In certain examples, the proximal end 328 of the second implant body portion 306 can include a retention element 356 configured to bias against at least a portion of a lacrimal canaliculus ampulla 252 (FIG. 2) when implanted. In this example, the retention element 356 projects proximally from the intersection between the first 304 and second 306 implant body portions, such as in an opposite direction as the extension of the dilator 350. When present and implanted in the ampulla 252, the retention element 356 can help secure a seated position of the graspable or other projection 332 against the punctal opening 212, 214.

In certain examples, the implant body 302 includes a first cavity 318 disposed near the proximal end 308. In this example, the first cavity 318 extends inward about 2 millimeters or less from the proximal end 308, and houses a first drug-releasing or other agent-releasing drug insert 322 to provide a sustained drug or other agent release to an eye. In some examples, the drug insert 322 can include a plurality of therapeutic agent inclusions 360, which can be distributed in a matrix 362. In some examples, the inclusions 360 can comprise a concentrated (e.g., crystalline) form of the therapeutic agent. In some examples, the matrix 362 can comprise a silicone matrix or the like, and the distribution of inclusions 360 within the matrix can be substantially homogenous or non-homogeneous. In some examples, the agent inclusions 360 can include droplets of oil, such as Latanoprost oil. In still other examples, the agent inclusions 360 can comprise solid particles, such as Bimatoprost particles in crystalline form. In some examples, the drug insert 322 comprises a urethane-based (e.g., polyurethane) polymer or copolymer comprising therapeutic agent inclusions deliverable into the eye or surrounding tissues. The inclusions can be of many sizes and shapes. For instance, the inclusions can include microparticles having dimensions on the order of about 1 micrometer to about 100 micrometers. Further discussion of drug-releasing or other agent-releasing drug inserts can be found in commonly-owned Utkhede et al., U.S. patent application Ser. No. 12/23,986, filed on Sep. 5, 2008, entitled "DRUG CORES FOR SUSTAINED RELEASE OF THERAPEUTIC AGENTS," published as U.S. Patent Application Publication No. 2009/0104243 on Apr. 23, 2009, and which is herein incorporated by reference in its entirety.

In various examples, the drug insert 322 can include a sheath body 366 disposed over at least a portion of the insert to define at least one insert exposed surface 368. The exposed surface 368 can be located at or near the proximal end 308 of the implant body 302, for example, thereby allowing direct contact with a tear or a tear film fluid and release of a drug or other therapeutic agent from the drug insert 322 over a sustained time period when the lacrimal implant 300 is inserted through the lacrimal punctum 212, 214 and into the associated canaliculus 208, 210.

FIG. 4 illustrates an example of a side view of another integral dilator 450 of an implant body 402 second portion 406 of a lacrimal implant 400. In this example, the dilator 450 narrows abruptly near a distal end 410 of the second portion 406. As shown, an implant body first portion 404 can include a first cavity 418 disposed near the proximal end 408. In this example, the first cavity 418 extends inward from the proximal end 408, and houses a first drug-releasing or other agent-releasing drug insert 422 to provide a sustained drug or other therapeutic agent release to an eye, for instance. In some examples, the drug or other therapeutic agent can released to an eye via an exposed, non-sheath covered surface 468 of the drug insert 422. In this example, the exposed surface 468 of the drug insert 422 is positioned above the proximal end 408 such that the drug insert 422 at least partially protrudes outside of the implant body 402.

In various examples, the outer surface 482 of the implant body 402 can be formed, or surface treated to be, generally smooth to inhibit bacteria from attaching to the lacrimal implant 400 and incubating. The generally smooth outer surface 482 can also prevent damage to the inner lining of the receiving anatomical tissue, such as a lacrimal punctum 212, 214 (FIG. 2) or associated canaliculus 208, 210 (FIG. 2), during implantation. As further discussed in commonly-owned Rapacki et al., U.S. patent application Ser. No. 12/283,002, filed Sep. 5, 2008, entitled "SURFACE TREATMENT OF IMPLANTS AND RELATED METHODS," issued as U.S. Pat. No. 8,210,902 on Jul. 3, 2012, and which is herein incorporated by reference in its entirety, the outer surface 482 of the implant body 402 can be surface treated to be generally smooth via a polishing process. The polishing process can include causing a molded implant body 402 to be impacted with polishing media during an ongoing period of time in which the body 402 is in an enlarged, swelled state. This can smooth one or more surfaces or edges of the implant body 402. In various examples, the polishing media can include at least some granules that are greater than about 3 millimeters in diameter.

In various examples, an antimicrobial coating 484 can be disposed on or impregnated in at least a portion of the outer surface 482 to further prevent bacteria growth on the implant body 402. In some examples, the antimicrobial coating 484 can include an agent selected from the group consisting of 2-bromo-2-nitropropane-1,3-diol, 5-bromo-5-nitro-1,3-dioxane, 7-ethyl bicyclooxazolidine, benzalkonium chloride, benzethonium chloride, benzoic acid, benzyl alcohol, boric acid, bronopol, cetylpyridinium chloride, chlorhexidine digluconate, chloroacetamide, chlorobutanol, chloromethyl isothiazolinone and methyl isothiazoline, dimethoxane, dimethyl oxazolidine, dimethyl hydroxymethyl pyrazole, chloroxylenol, dehydroacetic acid, diazolidinyl urea, dichlorobenzyl alcohol, DMDM hydantoin, ethyl alcohol, formaldehyde, glutaraldehyde, hexachlorophene, hexetidine, hexamethylenetramine, imidazolidinyl urea, iodopropynyl butylcarbamate, isothiazolinones, methenammonium chloride, methyldibromo glutaronitrile, MDM hydantoin, minocycline, ortho phenylphenol, p-chloro-m-cresol, parabens (butylparaben, ethylparaben, methylparaben), phenethyl alcohol, phenoxyethanol, piroctane olamine, polyaminopropyl biguanide, polymethoxy bicyclic oxazolidine, polyoxymethylene, polyquaternium-42, potassium benzoate, potassium sorbate, propionic acid, quaternium-15, rifampin, salicylic acid, selenium disulfide, sodium borate, sodium iodate, sodium hydroxymethylglycinate, sodium propionate, sodium pyrithione, sorbic acid, thimerosal, triclosan, triclocarban, undecylenic acid, zinc phenosulfonate, and zinc pyrithione. In some examples, the antimicrobial coating 484 can include a material selected from the group consisting of silver lactate, silver phosphate, silver citrate, silver acetate, silver benzoate, silver chloride, silver iodide, silver Iodate, silver nitrate, silver sulfadiazine, silver palmitate, or one or more mixtures thereof. In some examples, the antimicrobial coating 484 can include at least one of an antibiotic or an antiseptic. For instance, the antimicrobial coating 484 can include a temporary anesthetic lasting, on average, between a few hours and a day. In still other examples, the antimicrobial coating 484 can include a drug or other therapeutic agent used to treat an underlying disease, such as a bolus, for immediate effect.

Figure 5:
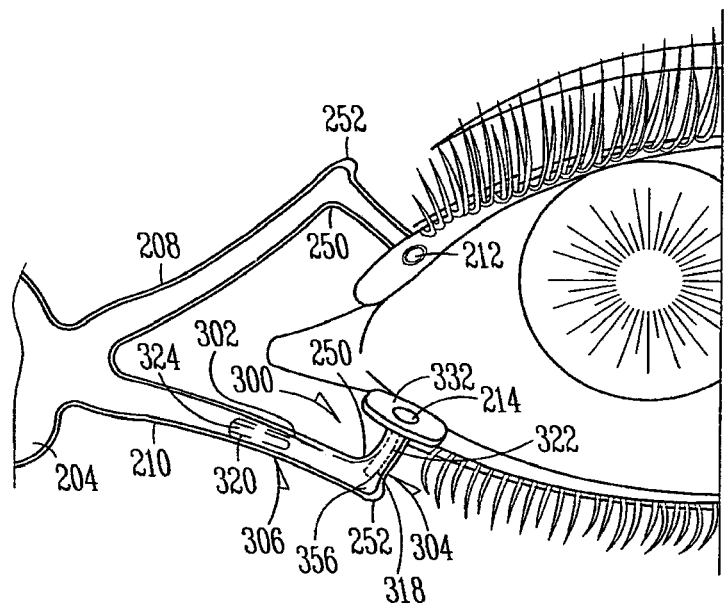
FIG. 5 illustrates an example of a schematic view of a lacrimal implant retained within a lacrimal punctum and associated canalicular anatomy, the lacrimal implant including at least one drug insert.

FIG. 5 illustrates an example of a schematic view of a lacrimal implant, such as the lacrimal implant 300 shown in FIG. 3, implanted in a lower lacrimal punctum 214 and associated canaliculus 210. In some examples, a lacrimal implant 300 can be implanted in an upper lacrimal punctum 212 and canaliculus 208. As discussed above, the lacrimal implant 300 can comprise an implant body 302 including first 304 and second 306 portions. In various examples, the implant body 302 can be configured such that, when implanted, at least a portion of the implant body 302 is biased against at least a portion of the lacrimal canaliculus 210 located at or more distal to a canaliculus curvature 250 to securely retain an implanted position of the implant 300. As shown, the first portion 304 can be configured to be inserted through the lacrimal punctum 214 and into the associated canaliculus 210 and rest between the punctal opening and a lacrimal canaliculus ampulla 252, while the second portion 306 can be configured to insert through the lacrimal punctum 214 and into the canaliculus 210 and rest between the ampulla 252 and the lacrimal sac 204. In certain examples, a retention element 356 projecting from a proximal end of the second portion 306 can be configured to bias into and against at least a portion of the ampulla 252 when implanted. In various examples, the first 304 and second 306 portions can be configured to bend, stretch or collapse, as desired, to maintain an adequate anatomical implanted fit without unduly stretching ocular anatomy.

In certain examples, to further secure an implant 300 within the lacrimal punctum 214 and canaliculus 210 or to make the implant body 302 adjustable in size, a hydrogel or other fluid swellable material can be disposed (e.g., coated) on an outer surface portion of the implant body 302. The fluid swellable material can effectively expand an outer surface diameter portion of the implant body 302 when implanted. In certain examples, the outer surface of the implant body 302 can include longitudinal channels or grooves or coatings of a wicking material so as to allow fluid flow around the implant body 302. Using one or a combination of these techniques, a lacrimal implant 300 can be configured to completely occlude or only partially occlude the lacrimal canaliculus 208, 210 when implanted therein. For instance, using the longitudinal channels or grooves in one or both of the first 304 or second 306 portions of the implant body 302 can allow diminished volumes or tear drainage can occur, potentially facilitating the release of a drug or other therapeutic agent from a drug insert.

Forceps or another insertion tool can be used to implant the lacrimal implant 300 through the lacrimal punctum 212, 214 and into the associated canaliculus 208, 210. In some examples, an insertion tool as discussed in commonly-owned De Juan, et al., U.S. patent application Ser. No. 12/231,984, filed on Sep. 5, 2008, entitled "INSERTION AND EXTRACTION TOOLS FOR LACRIMAL IMPLANTS," published as U.S. Patent Application Publication No. 2009/0105749 on Apr. 23, 2009, and which is herein incorporated by reference in its entirety, can be used to implant the lacrimal implant 300. In various examples, the second portion 306 of the implant body 302 can be advanced into the depth of the lacrimal canaliculus 208, 210 by manipulation of the inserter tool until a graspable or other projection 332, if present, can be seated against the punctal opening 212, 214. When it is desired to remove the lacrimal implant 300, the projection 332 can be grasped with the forceps, for example, and withdrawn from the punctal opening 212, 214.

In certain examples, the implant body 302 can include one or both of a first cavity 318 disposed near the proximal end 308 or a second cavity 320 disposed near the distal end 310. In this example, the first cavity 318 extends inward from the proximal end 308 of the first portion 304, and the second cavity 320 extends inward from the distal end 310 of the second portion 306. A first drug-releasing or other agent-releasing drug insert 322 can be disposed in the first cavity 318 to provide a sustained drug or other therapeutic agent release to the eye (e.g., to treat an infection, inflammation, glaucoma or other ocular disease or disorder), while a second drug-releasing or other agent-releasing drug insert 324 can be disposed in the second cavity 320 to provide a sustained drug or other therapeutic agent release to the nasal passage (e.g., to treat a sinus or allergy disorder) or inner ear system (e.g., to treat dizziness or a migraine), for example.

Figure 6A:
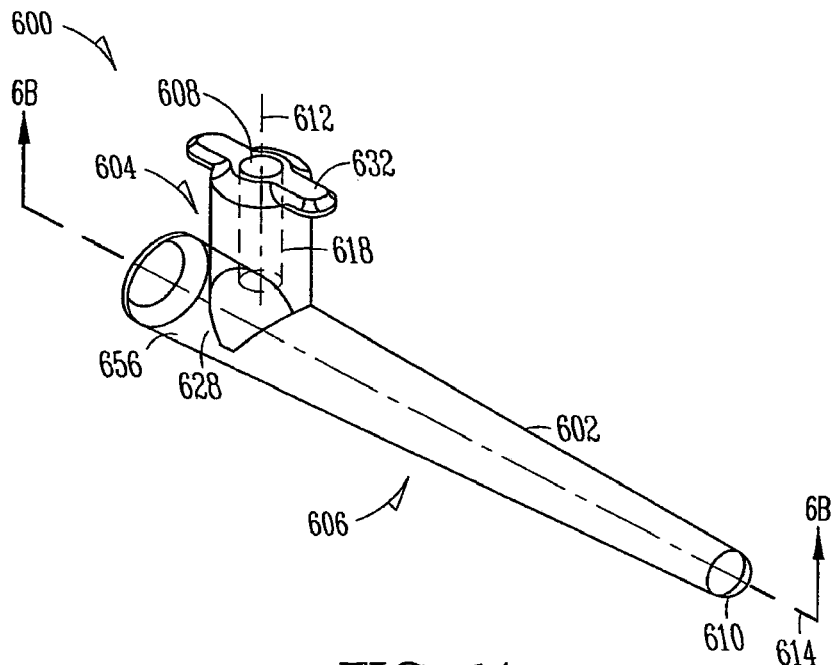
FIG. 6A illustrates an example of an isometric view of a lacrimal implant configured to be retained within a lacrimal punctum and associated canalicular anatomy, the lacrimal implant including a portion disposable within a lacrimal canaliculus ampulla.
Figure 6B:
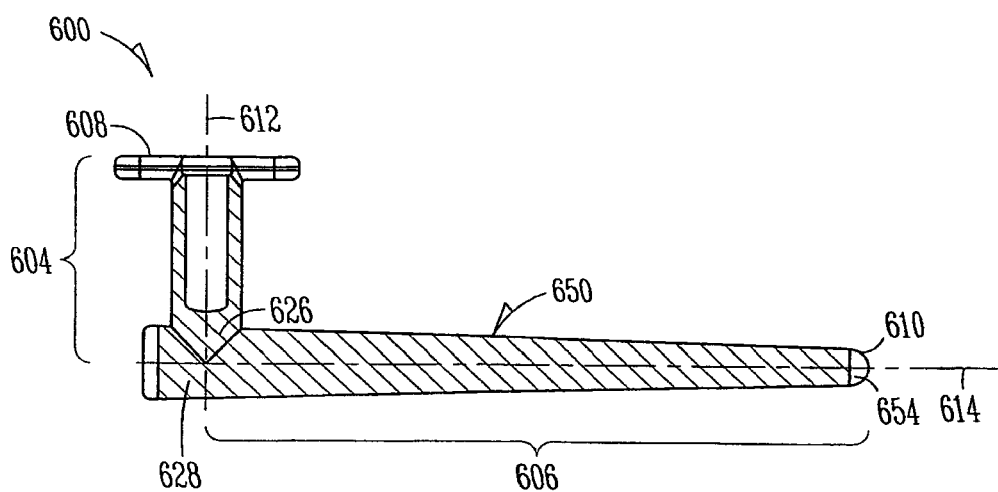
FIG. 6B illustrates an example of a cross-sectional view of a lacrimal implant taken along a line parallel to a longitudinal axis of the implant, such as along line 6B-6B.

FIGS. 6A-6B illustrate an example of another lacrimal implant 600 that is insertable through a lacrimal punctum 212, 214 and into the associated canaliculus 208, 210 (FIG. 2). In this example, the lacrimal implant 600 can comprises an implant body 602 including first 604 and second 606 portions, and can extend from a proximal end 608 of the first portion 604 to a distal end 610 of the second portion 606. The proximal end 608 can define a longitudinal proximal axis 612 and the distal end 610 can define a longitudinal distal axis 614. The implant body 600 can be configured such that, when implanted, an angled intersection of approximately 90 degrees exists between the proximal axis 612 and the distal axis 614 for biasing at least a portion of the implant body against at least a portion of the lacrimal canaliculus 208, 210 (FIG. 2) located at or more distal to a canaliculus curvature 250 (FIG. 2).

In this example, a proximal end 628 of the second implant body portion 606 can include a retention element 656 configured to bias against at least a portion of a lacrimal canaliculus ampulla 252 (FIG. 2) when implanted. In this example, the implant body 602 includes a first cavity 618, configured to receive a first drug-releasing or other agent-releasing drug insert, disposed near the proximal end 608 of the first implant body portion 604. Also in this example, the implant body 602 can include a graspable or other projection 632, such as a set of wings having a combined length of about 1 millimeter, for example, and extending laterally from the proximal end 308.

FIG. 6B illustrates an example of a cross-sectional view of the lacrimal implant 600 taken along a line parallel to a longitudinal axis of the implant, such as along line 6B-6B of FIG. 6A. As shown in FIG. 6B, a distal end 626 of the first portion 604 can be integral with the second portion 606 at or near a proximal end 628 of the second portion 606. In various examples, the second portion 606 can include a longitudinal length, as measured from the proximal axis 612 to the distal end 610, having a magnitude less than four times a longitudinal length of the first portion 604, as measured from the proximal end 608 to the distal axis 614. In some examples, the first portion can include a longitudinal length of about 1.54 millimeters and the second portion can include a longitudinal length of between about 4.5 millimeters to about 5.42 millimeters.

In various examples, the second portion 606 can comprise an integral dilator 650 to dilate anatomical tissue, such as one or both of the lacrimal punctum 212, 214 (FIG. 2) or associated canaliculus 208, 210, to a sufficient diameter as the lacrimal implant 600 is being implanted. In some examples, the second portion 606 tapers from a diameter of the proximal end of between about 0.50 millimeters to about 0.75 millimeters to a dilator tip 654 diameter of about 0.36 millimeters.

Figure 7A:
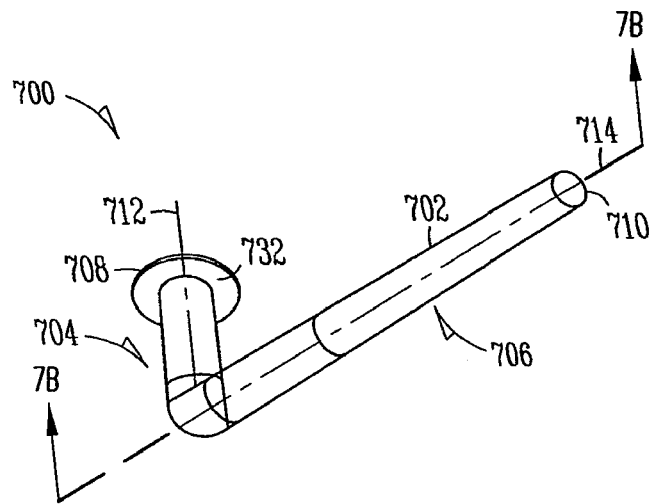
FIG. 7A illustrates an example of an isometric view of a lacrimal implant configured to be retained within a lacrimal punctum and associated canalicular anatomy, the lacrimal implant including an annular graspable projection.
Figure 7B:
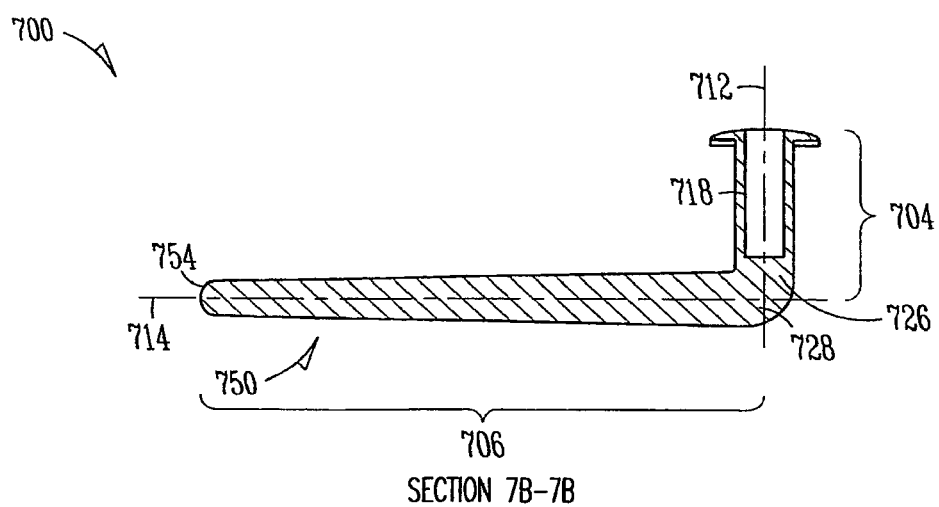
FIG. 7B illustrates an example of a cross-sectional view of a lacrimal implant taken along a line parallel to a longitudinal axis of the implant, such as along line 7B-7B.

FIGS. 7A-7B illustrate an example of another lacrimal implant 700 that is insertable through a lacrimal punctum 212, 214 and into the associated canaliculus 208, 210 (FIG. 2). In this example, the lacrimal implant 700 can comprises an implant body 702 including first 704 and second 706 portions, and can extend from a proximal end 708 of the first portion 704 to a distal end 710 of the second portion 706. The proximal end 708 can define a longitudinal proximal axis 712 and the distal end 710 can define a longitudinal distal axis 714. The implant body 700 can be configured such that, when implanted, an angled intersection of approximately 90 degrees exists between the proximal axis 712 and the distal axis 714 for biasing at least a portion of the implant body against at least a portion of the lacrimal canaliculus 208, 210 (FIG. 2) located at or more distal to a canaliculus curvature 250 (FIG. 2). As shown in the example of FIG. 7A, a smooth transition can exist between the first 704 and second 706 portions.

In this example, the implant body 702 includes a first cavity 718 configured to receive a first drug-releasing or other agent-releasing drug insert, disposed near the proximal end 708 of the first implant body portion 704. Also in this example, the implant body 702 can include a graspable or other projection 732, such as an annular projection extending laterally from, and completely around, the proximal end 708. In some examples, the graspable or other projection 732 includes a partially trimmed projection having a trimmed width of about 0.75 millimeters and extending varying amounts around the proximal end 708.

FIG. 7B illustrates an example of a cross-sectional view of the lacrimal implant 700 taken along a line parallel to a longitudinal axis of the implant, such as along line 7B-7B of FIG. 7A. As shown in FIG. 7B, a distal end 726 of the first portion 704 can be integral with the second portion 706 at or near a proximal end 728 of the second portion 706. In various examples, the second portion 706 can include a longitudinal length, as measured from the proximal axis 712 to the distal end 710, having a magnitude less than four times a longitudinal length of the first portion 704, as measured from the proximal end 708 to the distal axis 714. In some examples, the first portion can include a longitudinal length of about 1.5 millimeters and the second portion can include a longitudinal length of about 5 millimeters.

In various examples, the second portion 706 can comprise an integral dilator 750 to dilate anatomical tissue, such as one or both of the lacrimal punctum 212, 214 (FIG. 2) or associated canaliculus 208, 210, to a sufficient diameter as the lacrimal implant 700 is being implanted. In some examples, the second portion 706 tapers from a diameter of the proximal end of about 0.46 millimeters to a dilator tip 754 diameter of about 0.36 millimeters.

Figure 8A:
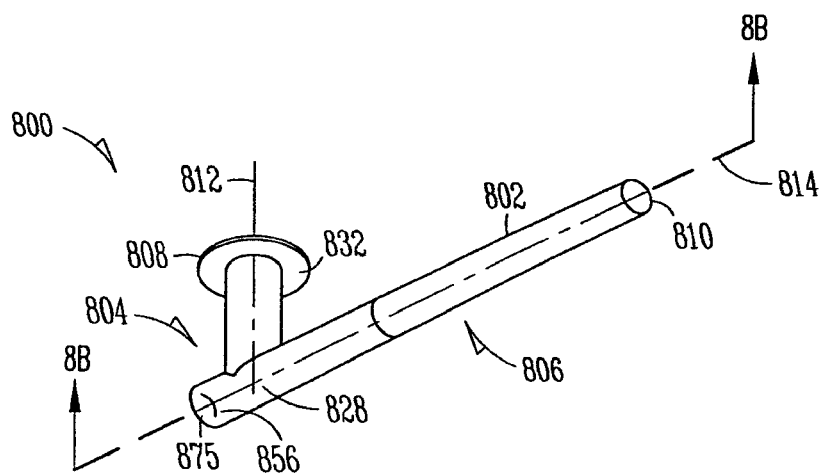
FIG. 8A illustrates an example of an isometric view of a lacrimal implant configured to be retained within a lacrimal punctum and associated canalicular anatomy, the lacrimal implant including a portion disposable within a lacrimal canaliculus ampulla and including an insertion-facilitating depression.
Figure 8B:
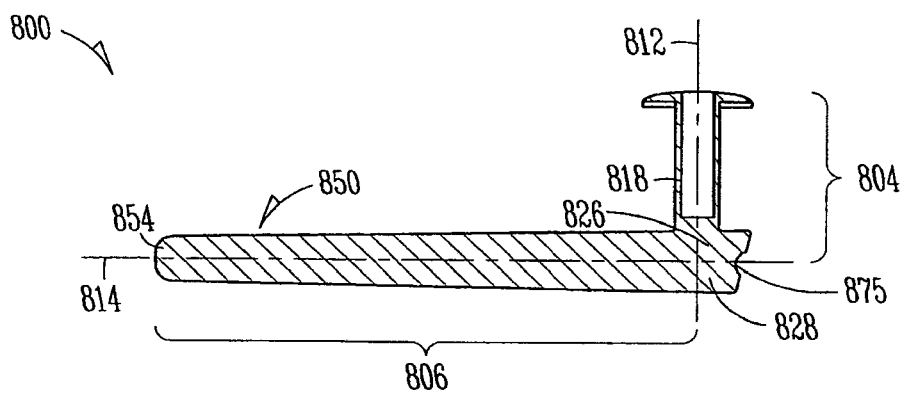
FIG. 8B illustrates an example of a cross-sectional view of a lacrimal implant taken along a line parallel to a longitudinal axis of the implant, such as along line 8B-8B.

FIGS. 8A-8B illustrate an example of another lacrimal implant 800 that is insertable through a lacrimal punctum 212, 214 and into the associated canaliculus 208, 210 (FIG. 2). In this example, the lacrimal implant 800 can comprises an implant body 802 including first 804 and second 806 portions, and can extend from a proximal end 808 of the first portion 804 to a distal end 810 of the second portion 806. The proximal end 808 can define a longitudinal proximal axis 812 and the distal end 810 can define a longitudinal distal axis 814. The implant body 800 can be configured such that, when implanted, an angled intersection of approximately 90 degrees exists between the proximal axis 812 and the distal axis 814 for biasing at least a portion of the implant body against at least a portion of the lacrimal canaliculus 208, 210 (FIG. 2) located at or more distal to a canaliculus curvature 250 (FIG. 2).

In this example, a proximal end 828 of the second implant body portion 806 can include a retention element 856 configured to bias against at least a portion of a lacrimal canaliculus ampulla 252 (FIG. 2) when implanted. The retention element 856 can include an insertion-facilitating depression 875 or other gripping means to aid in one or both of implant insertion or removal. In this example, the implant body 802 includes a first cavity 818 configured to receive a first drug-releasing or other agent-releasing drug insert, disposed near the proximal end 808 of the first implant body portion 804. Also in this example, the implant body 802 can include a graspable or other projection 832, such as an annular projection extending laterally from, and completely around, the proximal end 808. In some examples, the graspable or other projection 832 includes a partially trimmed projection extending varying amounts around the proximal end 808.

FIG. 8B illustrates an example of a cross-sectional view of the lacrimal implant 800 taken along a line parallel to a longitudinal axis of the implant, such as along line 8B-8B of FIG. 8A. As shown in FIG. 8B, a distal end 826 of the first portion 804 can be integral with the second portion 806 at or near the proximal end 828 of the second portion 806. In various examples, the second portion 806 can include a longitudinal length, as measured from the proximal axis 812 to the distal end 810, having a magnitude less than four times a longitudinal length of the first portion 804, as measured from the proximal end 808 to the distal axis 814. In some examples, the first portion can include a longitudinal length of between about 1.725 millimeters to about 1.77 millimeters and the second portion can include a longitudinal length of between about 4.77 millimeters to about 5 millimeters.

In various examples, the second portion 806 can comprise an integral dilator 850 to dilate anatomical tissue, such as one or both of the lacrimal punctum 212, 214 (FIG. 2) or associated canaliculus 208, 210, to a sufficient diameter as the lacrimal implant 800 is being implanted. In some examples, the second portion 806 tapers from a diameter of the proximal end 828 of about 0.46 millimeters to a dilator tip 854 diameter of about 0.36 millimeters.

Figure 9:
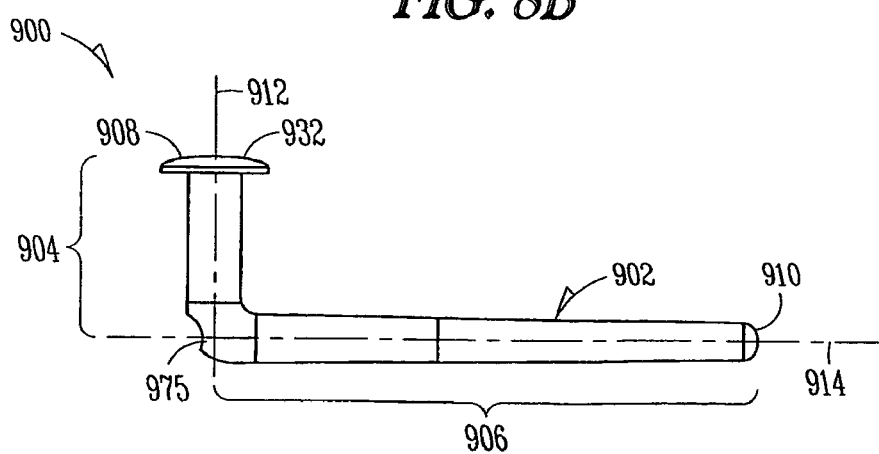
FIG. 9 illustrates an example of side view of a lacrimal implant configured to be retained within a lacrimal punctum and associated canalicular anatomy, the lacrimal implant including an insertion-facilitating depression.

FIG. 9 illustrates an example of another lacrimal implant 900 that is insertable through a lacrimal punctum 212, 214 and into the associated canaliculus 208, 210 (FIG. 2). In this example, the lacrimal implant 900 can comprises an implant body 902 including first 904 and second 906 portions, and can extend from a proximal end 908 of the first portion 904 to a distal end 910 of the second portion 906. The proximal end 908 can define a longitudinal proximal axis 912 and the distal end 910 can define a longitudinal distal axis 914. The implant body 900 can be configured such that, when implanted, an angled intersection of approximately 90 degrees exists between the proximal axis 912 and the distal axis 914 for biasing at least a portion of the implant body against at least a portion of the lacrimal canaliculus 208, 210 (FIG. 2) located at or more distal to a canaliculus curvature 250 (FIG. 2).

As shown, a smooth transition can exist between the first 904 and second 906 portions. In this example, the smooth transition can include an insertion-facilitating depression 975 or other gripping means to aid in one or both of implant insertion or removal. Also in this example, the implant body 902 can include a graspable or other projection 932, such as an annular projection extending laterally from, and completely around, the proximal end 908. In some examples, the graspable or other projection 932 includes a partially trimmed projection extending varying amounts around the proximal end 908.

Figure 10A:
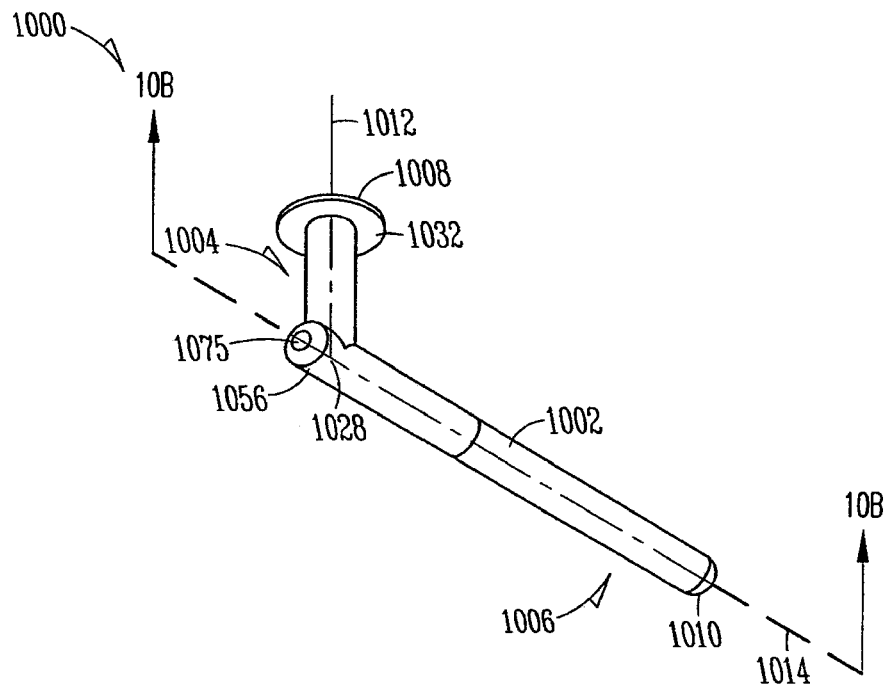
FIG. 10A illustrates an example of an isometric view of a lacrimal implant configured to be retained within a lacrimal punctum and associated canalicular anatomy, the lacrimal implant including a portion disposable within a lacrimal canaliculus ampulla.
Figure 10B:
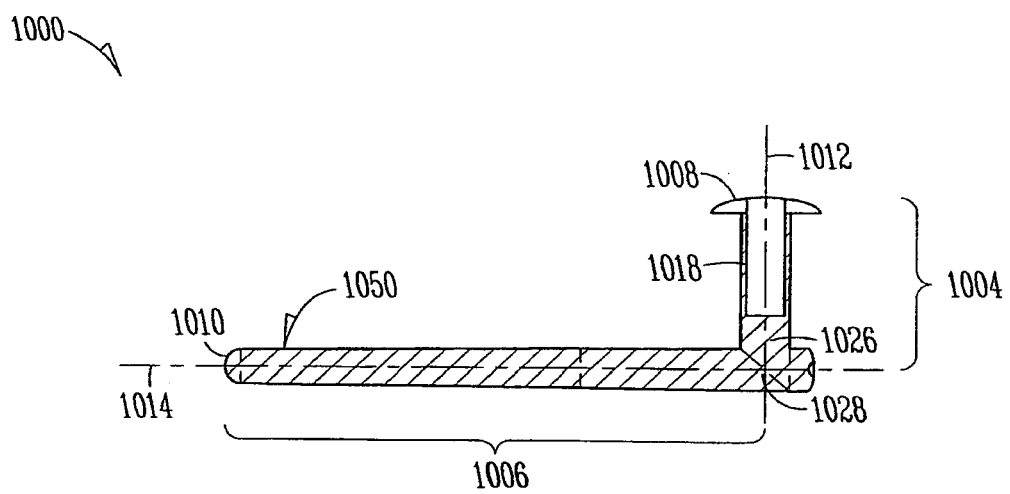
FIG. 10B illustrates an example of a cross-sectional view of a lacrimal implant taken along a line parallel to a longitudinal axis of the implant, such as along line 10B-10B.
Figure 11:
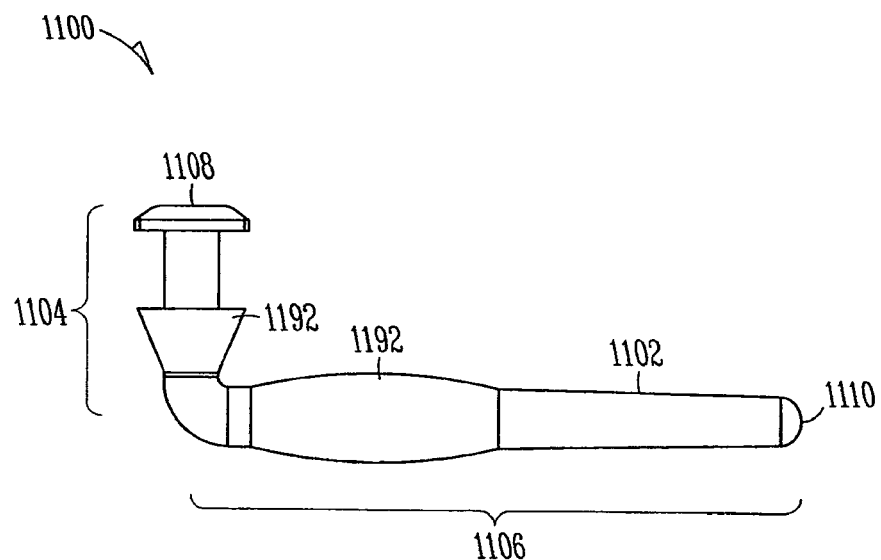
FIGS. 11-13 illustrate examples of a side view of various lacrimal implants configured to be retained within a lacrimal punctum and associated canalicular anatomy, each lacrimal implant including at least one intermediately-disposed retainment projection.
Figure 12:
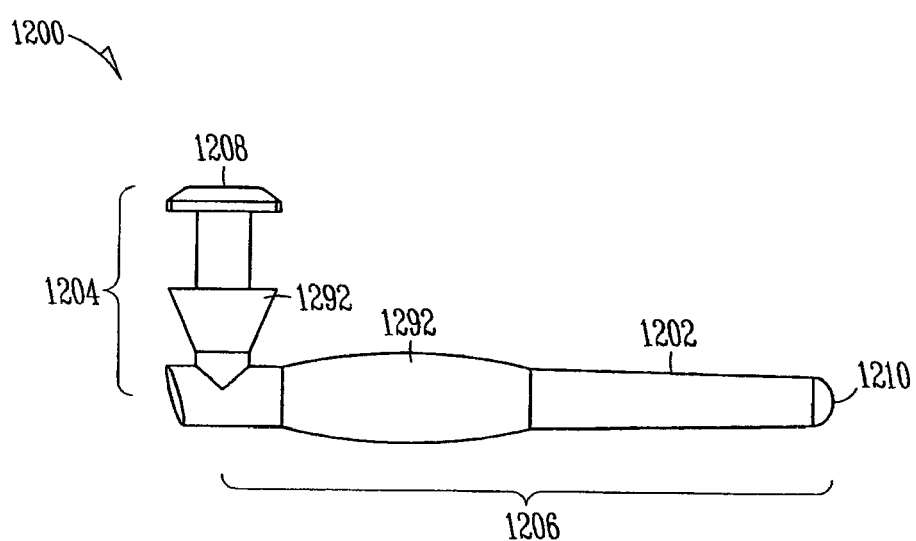
Figure 13:
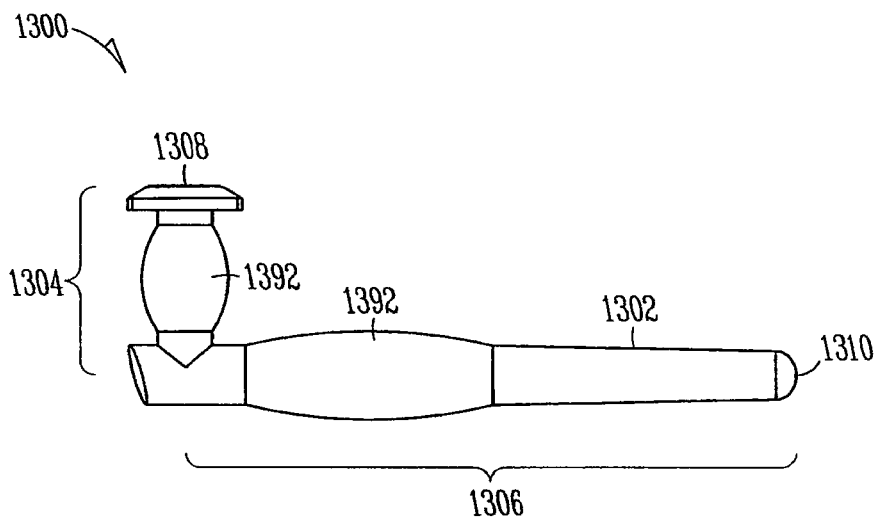
Figure 14:
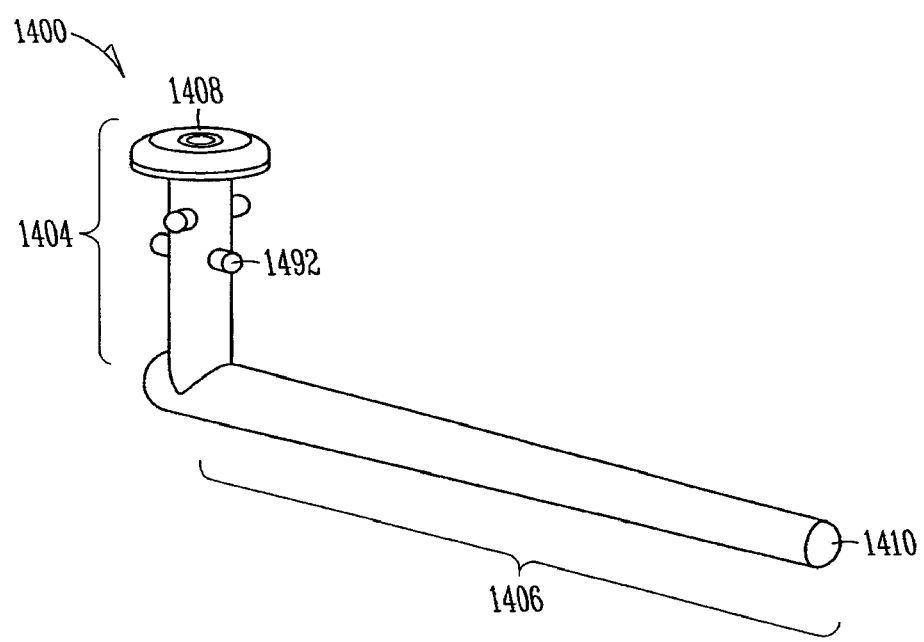
FIGS. 14-17 illustrate examples of an isometric view of various lacrimal implants configured to be retained within a lacrimal punctum and associated canalicular anatomy, each lacrimal implant including at least one intermediately-disposed retainment projection.
Figure 15:
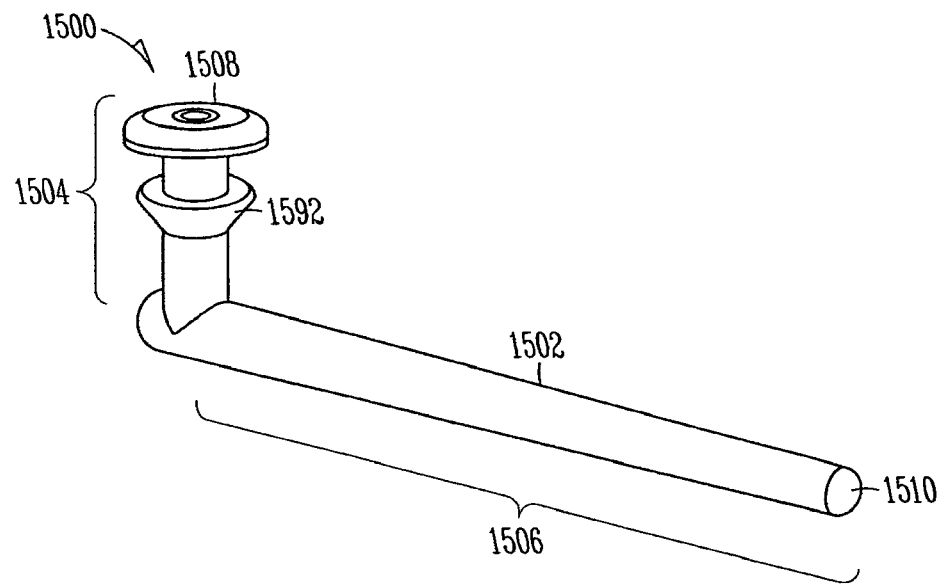
Figure 16:
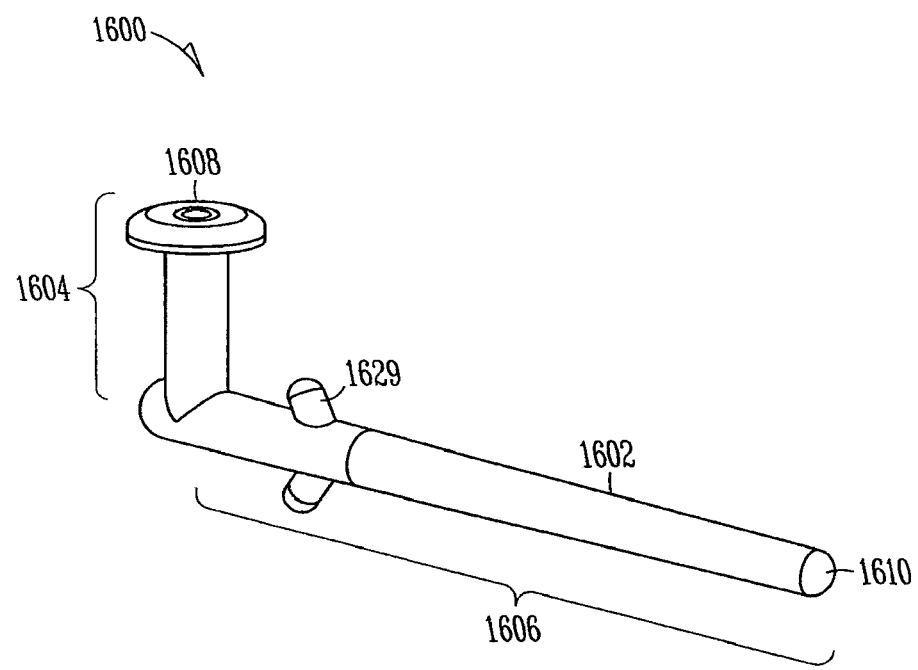
Figure 17:
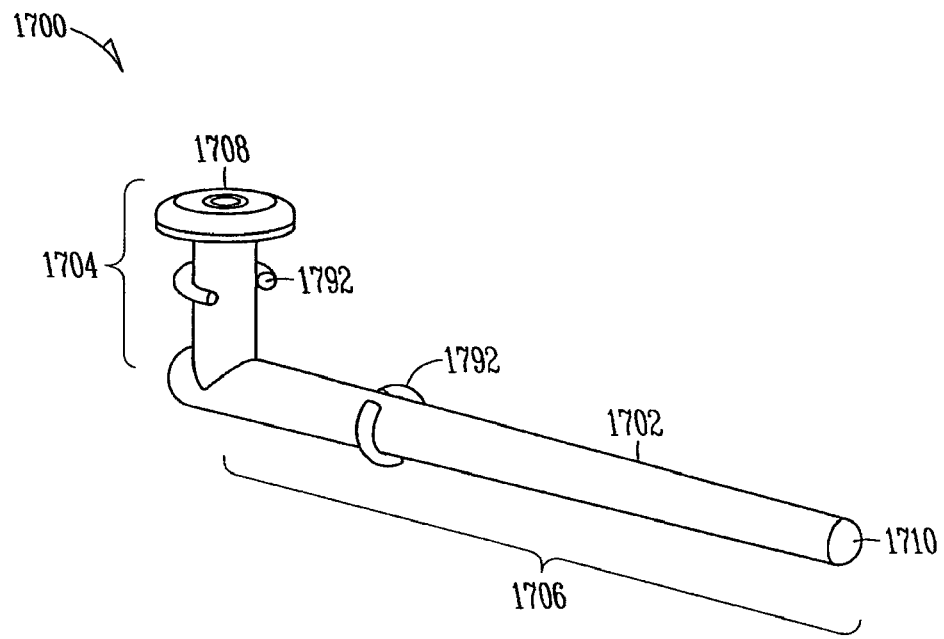

FIGS. 10A-10B illustrate an example of another lacrimal implant 1000 that is insertable through a lacrimal punctum 212, 214 and into the associated canaliculus 208, 210 (FIG. 2). In this example, the lacrimal implant 1000 can comprises an implant body 1002 including first 1004 and second 1006 portions, and can extend from a proximal end 1008 of the first portion 1004 to a distal end 1010 of the second portion 1006. The proximal end 1008 can define a longitudinal proximal axis 1012 and the distal end 1010 can define a longitudinal distal axis 1014. The implant body 1000 can be configured such that, when implanted, an angled intersection of approximately 90 degrees exists between the proximal axis 1012 and the distal axis 1014 for biasing at least a portion of the implant body against at least a portion of the lacrimal canaliculus 208, 210 (FIG. 2) located at or more distal to a canaliculus curvature 250 (FIG. 2).

In this example, a proximal end 1028 of the second implant body portion 1006 can include a retention element 1056 configured to bias against at least a portion of a lacrimal canaliculus ampulla 252 (FIG. 2) when implanted. The retention element 1056 can include an insertion-facilitating depression 1075 or other gripping means to aid in one or both of implant insertion or removal. In this example, the implant body 1002 includes a first cavity 1018 configured to receive a first drug-releasing or other agent-releasing drug insert, disposed near the proximal end 1008 of the first implant body portion 1004. Also in this example, the implant body 1002 can include a graspable or other projection 1032, such as an annular projection having a diameter of about 1.3 millimeters extending laterally from, and completely around, the proximal end 1008. In some examples, the graspable or other projection 1032 includes a partially trimmed projection extending varying amounts around the proximal end 1008.

FIG. 10B illustrates an example of a cross-sectional view of the lacrimal implant 1000 taken along a line parallel to a longitudinal axis of the implant, such as along line 10B-10B of FIG. 10A. As shown in FIG. 10B, a distal end 1026 of the first portion 1004 can be integral with the second portion 1006 at or near a proximal end 1028 of the second portion 1006. In various examples, the second portion 1006 can include a longitudinal length, as measured from the proximal axis 1012 to the distal end 1010, having a magnitude less than four times a longitudinal length of the first portion 1004, as measured from the proximal end 1008 to the distal axis 1014. In some examples, the first portion can include a longitudinal length of about 1.5 millimeters and the second portion can include a longitudinal length of about 5 millimeters.

In various examples, the second portion 1006 can comprise an integral dilator 1050 to dilate anatomical tissue, such as one or both of the lacrimal punctum 212, 214 (FIG. 2) or associated canaliculus 208, 210, to a sufficient diameter as the lacrimal implant 1000 is being implanted. In some examples, the second portion 1006 tapers from a proximal end 1028 diameter of about 0.46 millimeters to a dilator tip 1054 diameter of about 0.36 millimeters.

FIGS. 11-17 illustrate examples of other lacrimal implants 1100, 1200, 1300, 1400, 1500, 1600, 1700 that are insertable through a lacrimal punctum 212, 214 and into the associated canaliculus 208, 210 (FIG. 2). In these examples, each lacrimal implant 1100, 1200, 1300, 1400, 1500, 1600, 1700 can comprises an implant body 1102, 1202, 1302, 1402, 1502, 1602, 1702 including first 1104, 1204, 1304, 1404, 1504, 1604, 1704 and second 1106, 1206, 1306, 1406, 1506, 1606, 1706 portions, and can extend from a proximal end 1108, 1208, 1308, 1408, 1508, 1608, 1708 of the first portion 1104, 1204, 1304, 1404, 1504, 1604, 1704 to a distal end 1110, 1210, 1310, 1410, 1510, 1610, 1710 of the second portion 1106, 1206, 1306, 1406, 1506, 1606, 1706. Each implant body 1102, 1202, 1302, 1402, 1502, 1602, 1702 can include at least one intermediately-disposed retainment projection 1192, 1292, 1392, 1492, 1592, 1692, 1792 to potentially further secure an implanted position of the lacrimal implants. The intermediately-disposed retainment projections 1192, 1292, 1392, 1492, 1592, 1692, 1792 can be positioned on one or both of the first 1104, 1204, 1304, 1404, 1504, 1604, 1704 or second 1106, 1206, 1306, 1406, 1506, 1606, 1706 implant body portions, and can take the form of annular, semi-annular, column-like or barrel-like projection. The intermediately-disposed retainment projections 1192, 1292, 1392, 1492, 1592, 1692, 1792 can include a cross-sectional size greater than an adjacent implant body portion and can slightly deform a portion of a canalicular wall to provide the added securement.

It is believed that the occlusion of the lower lacrimal canaliculus 210, for example, by a lacrimal implant may cause back pressure to build-up within the canaliculus 210, thereby urging the implant from an implanted position. It is thought that this back pressure could, for example, occur during a blink (where tears are being pumped from an anterior surface of the eye down a drainage system) or a sneeze (where pressure is emanating up from the pulmonary system). Accordingly, one of more of the additional retention features now shown in the form of at least one intermediately-disposed retainment projection 1192, 1292, 1392, 1492, 1592, 1692, 1792 may be used to prevent implant migration and further secure an implanted lacrimal implant position. These additional retention features can be designed to prevent migration in the proximal direction while not increasing implant implantation difficulty.

Figure 18:
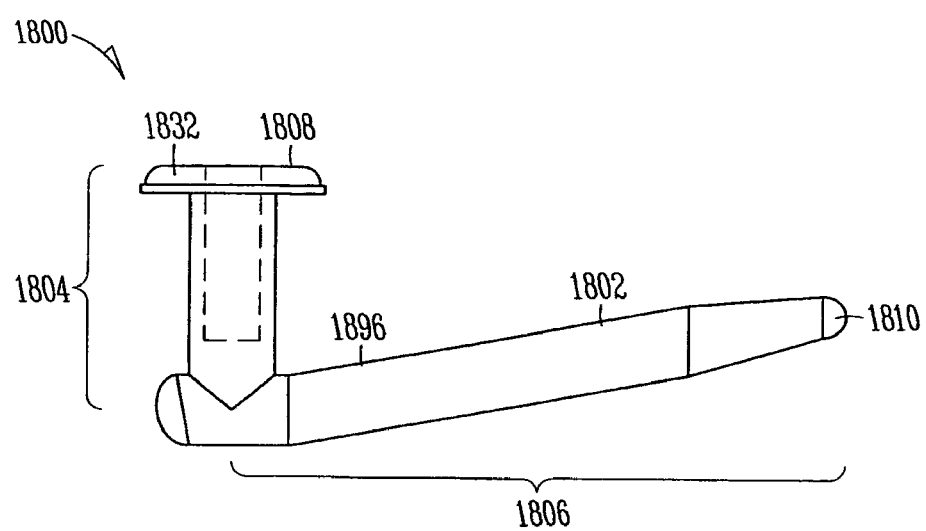
FIGS. 18-19 illustrate examples of a side view of lacrimal implants configured to be retained within a lacrimal punctum and associated canalicular anatomy, each lacrimal implant including a non-perpendicular angled intersection between first and second implant body portions.
Figure 19:
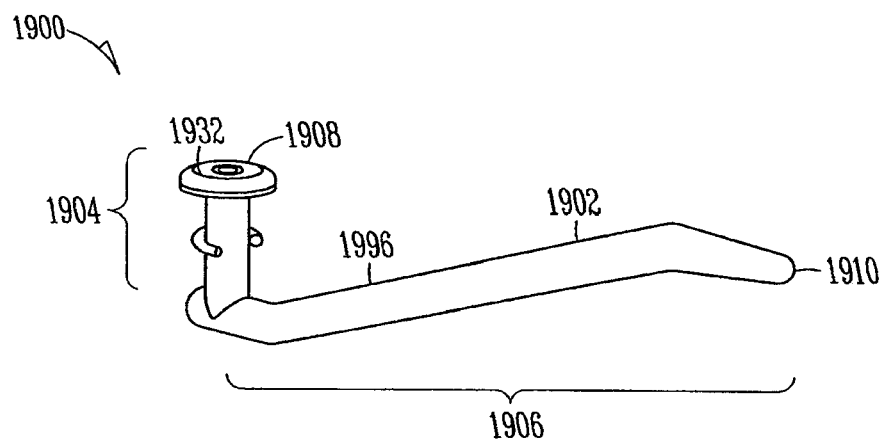

FIGS. 18-19 illustrate examples of other lacrimal implants 1800, 1900 that are insertable through a lacrimal punctum 212, 214 and into the associated canaliculus 208, 210 (FIG. 2). In these examples, each lacrimal implant 1800, 1900 can comprise an implant body 1802, 1902 including first 1804, 1904 and second 1806, 1906 portions, and can extend from a proximal end 1808, 1908 of the first portion 1804, 1904 to a distal end 1810, 1910 of the second portion 1806, 1906. As shown, an intermediate portion 1896, 1996 of each implant body 1802, 1902 can be angled relative to one or both of the first 1804, 1904 or second 1806, 1906 implant body portions to potentially further secure an implanted position of the lacrimal implants.

It is believed that the angling of the intermediate portion 1896, 1996 may help capture the anatomy of the lacrimal punctum 212, 214 and canaliculus 208, 210 to keep the lacrimal implants 1800, 1900 in an implanted position, such as via a directional force applied by the angling against the lacrimal canaliculus. This directional force can be designed to continuously urge a feedback or other projection 1832, 1932 flush with the punctum 212, 214.

Figure 20:
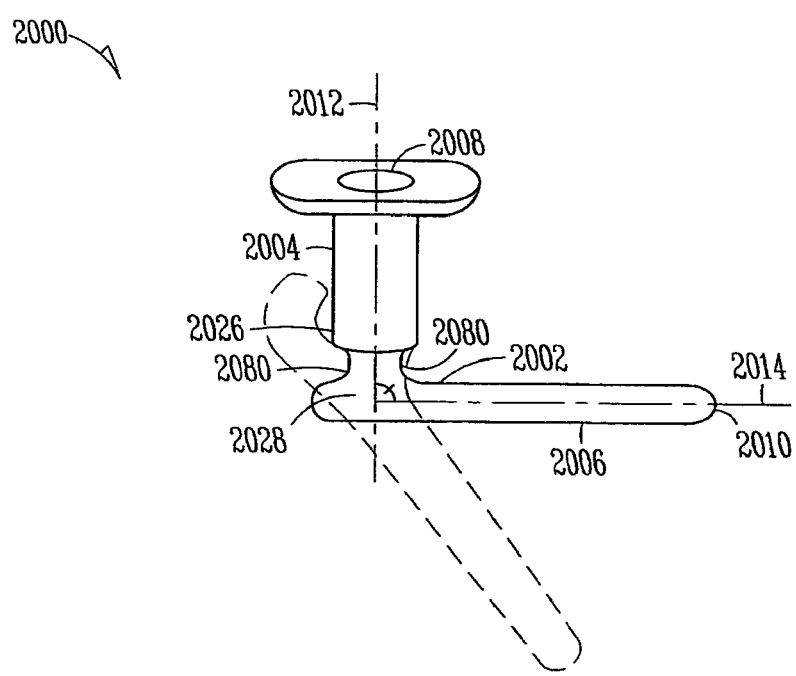
FIG. 20 illustrates an example of an isometric view of a lacrimal implant configured to be retained within a lacrimal punctum and associated canalicular anatomy, the lacrimal implant including one or more material cutouts.

FIG. 20 illustrates an example of another lacrimal implant 2000 that is insertable through a lacrimal punctum 212, 214 and into the associated canaliculus 208, 210 (FIG. 2). In this example, the lacrimal implant 2000 can comprises an implant body 2002 including first 2004 and second 2006 portions, and can extend from a proximal end 2008 of the first portion 2004 to a distal end 2010 of the second portion 2006. The proximal end 2008 can define a longitudinal proximal axis 2012 and the distal end 2010 can define a longitudinal distal axis 2014. The implant body 2000 can be configured such that, when implanted, an angled intersection of approximately 90 degrees exists between the proximal axis 2012 and the distal axis 2014 for biasing at least a portion of the implant body against at least a portion of a lacrimal canaliculus 208, 210 (FIG. 2) located at or more distal to a canaliculus curvature 250 (FIG. 2). In various examples, a distal end 2026 of the first portion 2004 can be integral with the second portion 2006 at or near a proximal end 2028 of the second portion 2006.

In this example, one or more material cutouts 2080 are made in an outer surface of the implant body 2002. As a result, the angled intersection between the proximal axis 2012 and the distal axis 2014 can become more linearly aligned during implant, as shown in phantom, to facilitate insertion through the lacrimal punctum 212, 214 and into the associated canaliculus 208, 210.

FIGS. 21A-21B and 22A-22B illustrate examples of a side view of other lacrimal implants 2100, 2200 that are insertable through a lacrimal punctum 212, 214 and into the associated canaliculus 208, 210 (FIG. 2). In these examples, each lacrimal implant 2100, 2200 can comprises an implant body 2102, 2202 including first 2104, 2204 and second 2106, 2206 portions, and can extend from a proximal end 2108, 2208 of the first portion 2104, 2204 to a distal end 2110, 2210 of the second portion 2106, 2206. Each second portion 2106, 2206 can include one or more arm members 2170, 2270 movable between a first configuration, in which the one or more arm members 2170, 2270 are adjacent the implant body, and a second configuration, in which the one or more arm members 2170, 2270 laterally extend from a side of the implant body. In the first configuration, the one or more arm members 2170, 2270 facilitate insertion of the lacrimal implant through the lacrimal punctum 212, 214 and into the associated canaliculus 208, 210 by providing a narrow profile. In the second configuration, the one or more arm members 2170, 2270 laterally extend to fill at least one of a lacrimal canaliculus ampulla 252 (FIG. 2) or the canaliculus 208, 210 when implanted. Optionally, the one or more arm members 2170, 2270 can include a fluid swellable material, such as hydrogel, to further secure an implanted lacrimal implant within the lacrimal ampulla 252 or canaliculus 208, 210 when hydrated.

In some examples, the one or more arm members 2170, 2270 can be incorporated into a mold that is also used to form the implant body 2102, 2202. The one or more arm members 2170, 2270 can alternatively be attached by molding or gluing onto an existing implant body 2102, 2202. Different thicknesses and shapes for the one or more arm members 2170, 2270 can be employed for different stiffness and securing/removal characteristics. Beyond hydrogel, the one or more arm members 2170, 2270 can be made of other materials, such as those used for the haptics on the intraocular lenses or the like.

FIG. 23A-23B illustrate an example of a side view of another lacrimal implant 2300 that is insertable through a lacrimal punctum 212, 214 and into the associated canaliculus 208, 210 (FIG. 2). In this example, the lacrimal implant 2300 can comprises an implant body 2302 including first 2304 and second 2306 portions, and can extend from a proximal end 2308 of the first portion 2304 to a distal end 2310 of the second portion 2306. The second portion 2306 can be surrounded, at least in part, by an expandable retention element (e.g., an inflatable balloon) 2372, which is configured to bias the second portion 2306 away from a lacrimal canaliculus wall upon expansion.

In some examples, the expandable retention element 2372 contains or can be inflated by an agent to be delivered to a tissue of the eye or nasolacrimal system. In some examples, the expandable retention element 2372 can employ one or more balloons which are separate from any drug insert or other agent retaining structure. The one or more balloons may optionally be similar to those used on balloon catheters, with an inflation lumen or the like optionally being included in an implant insertion tool so as to allow controlled inflation of the balloon. In such an example, the lacrimal implant 2300 may be inserted with the balloons deflated, as shown in FIG. 23A. Once the lacrimal implant 2300 is in place, the balloons can then inflated to secure an implanted position of the implant, as shown in FIG. 23B.

The balloons can also be deflatable to make removal of the lacrimal implant 2300 easier. The balloons can optionally partially or substantially conform to variations in the size and shape of the canaliculus 208, 210. Alternative examples of balloons may be inflated by swelling of a material disposed within the balloon, such as swelling of a hydrogel by absorption of water through perforations or openings in the balloon. The one or more balloons can be annular structures disposed around the supporting implant body, or may be disposed eccentrically about an axis of the implant body. As illustrated in FIG. 23B, the balloons may be disposed sufficiently distal to reside within or adjacent a horizontal portion of the tear drainage duct, within or adjacent a lacrimal ampulla of the tear drainage system, or the like. Alternative examples can include one or more balloons which are more proximal.

FIG. 24 illustrates an example of a schematic view of another lacrimal implant 2400 implanted through a lower lacrimal punctum 214 and into the associated canaliculus 210. The lacrimal implant 2400 can comprise an implant body 2402 including first 2404 and second 2406 portions. In various examples, the implant body 2402 can be configured such that, when implanted, at least a portion of the implant body 2402 is biased against at least a portion of the lacrimal canaliculus 210 located at or more distal to a canaliculus curvature 250 to securely retain an implanted position of the implant 2400. In this example, the second portion 2406 includes a longitudinal length less than about 2 millimeters, such as a size greater than a diameter of the first portion 2404, but less than 2 millimeters. Also in this example, the implant body 2402 can include a graspable or other projection 2432, such as extending laterally at least partially around a proximal end of the first implant body portion 2404.

Figure 25A:
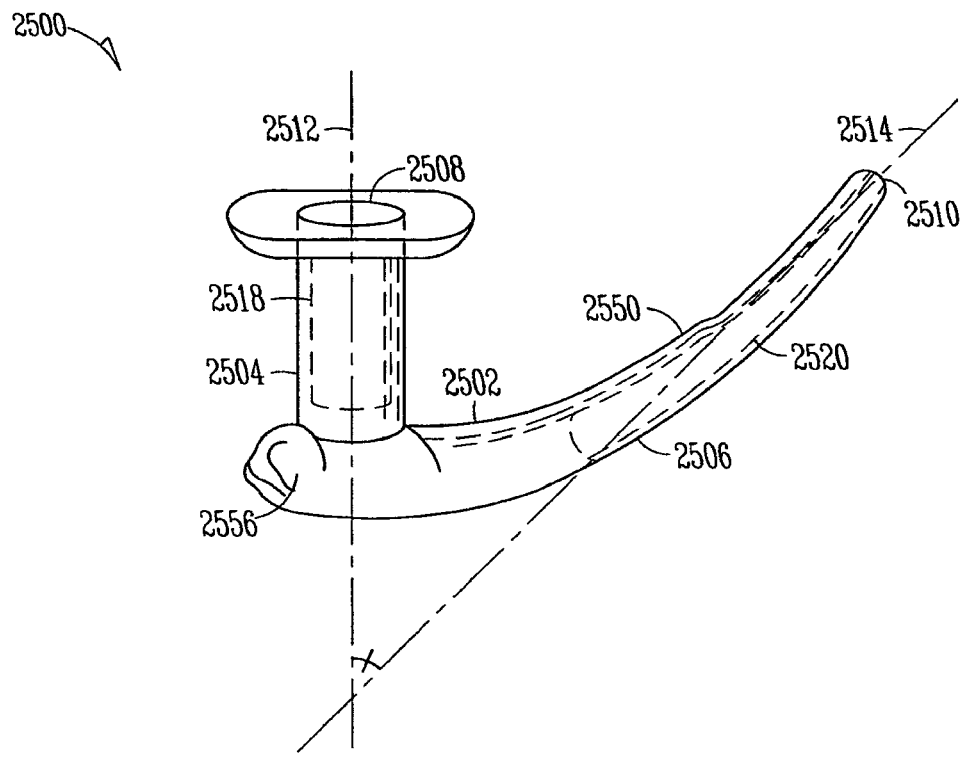
FIGS. 25A-25B illustrate examples of an isometric view of lacrimal implants configured to be retained within a lacrimal punctum and associated canalicular anatomy, each lacrimal implant including an implant body portion having a generally concave shape.
Figure 25B:
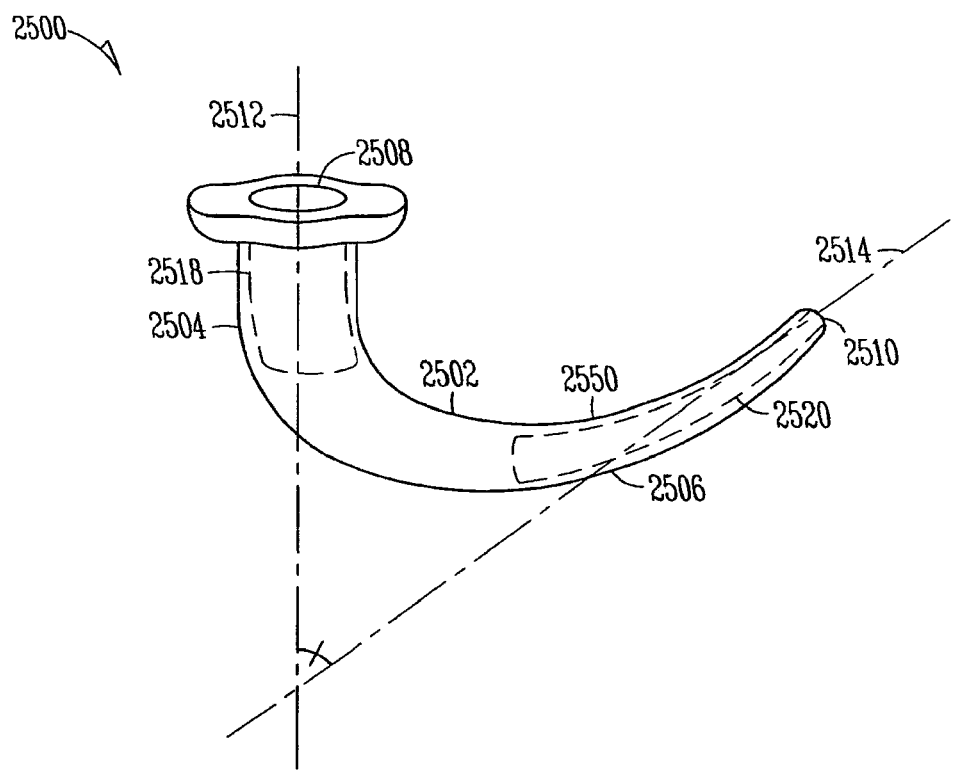

FIGS. 25A-25B illustrate examples of another lacrimal implant 2500 that is insertable through a lacrimal punctum 212, 214 and into the associated canaliculus 208, 210 (FIG. 2). In these examples, the lacrimal implant 2500 can comprise an implant body 2502 including first 2504 and second 2506 portions, and can extend from a proximal end 2508 of the first portion 2504 to a distal end 2510 of the second portion 2506. The implant body can include a general shape, which can generally match the anatomical features of a canaliculus 208, 210 to provide patient comfort and secure retainment, for example. The proximal end 2508 can define a longitudinal proximal axis 2512 and the distal end 2510 can define a longitudinal distal axis 2514. The implant body 2502 can be configured such that, when implanted, an angled intersection of between 45-90 degrees exists between the proximal axis 2512 and the distal axis 2514 such as for biasing at least a portion of the implant body 2502 against at least a portion of a lacrimal canaliculus 208, 210 (FIG. 2) located at or more distal to a canaliculus curvature 250 (FIG. 2).

Figure 26:
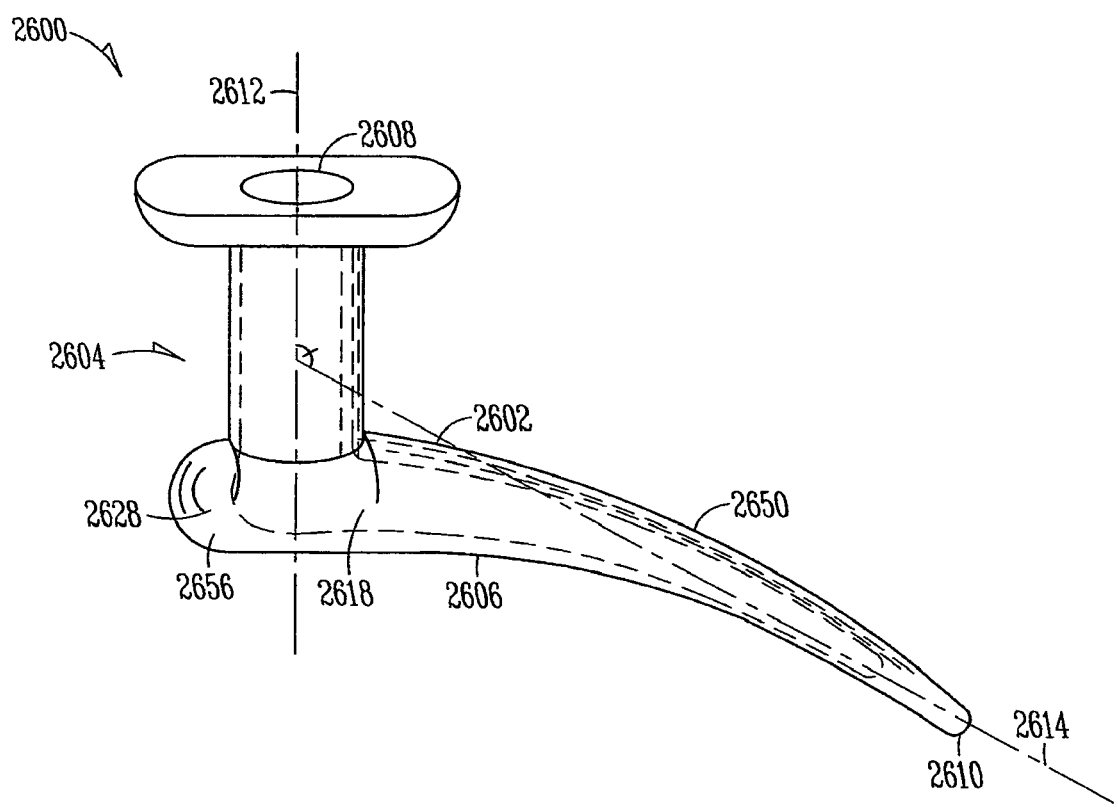
FIG. 26 illustrates an example of an isometric view of a lacrimal implant configured to be retained within a lacrimal punctum and associated canalicular anatomy, the lacrimal implant including an implant body portion having a generally convex shape.

In the examples of FIGS. 25A-25B, the implant body 2502 includes both of a first cavity 2518 disposed near the proximal end 2508 and a second cavity 2520 disposed near the distal end 2510. The first cavity 2518 extends inward from the proximal end 2508 of the first portion 2504, and the second cavity 2520 extends inward from the distal end 2510 of the second portion 2506. A first drug-releasing or other agent-releasing drug insert can be disposed in the first cavity 2518 to provide a sustained drug or other therapeutic agent release to an eye, while a second drug-releasing or other agent-releasing drug insert can be disposed in the second cavity 2520 to provide a sustained drug or other therapeutic agent release to a nasal passage or inner ear system, for example. In some examples, the first cavity 2518 can extend inward from the proximal end 2508 of the first portion 2504 to a position near the distal end 2510 of the second portion 2506, such as is shown in FIG. 26, and is filled with a first drug-releasing or other agent-releasing drug insert. In some examples, the second cavity 2520 can extend inward from the distal end 2510 of the second portion 2506 to a position near the proximal end 2508 of the first portion 2504 and is filled with a second drug-releasing or other agent-releasing drug insert.

In certain examples, the second portion 2506 comprises an integral dilator 2550 to dilate anatomical tissue, such one or both of the lacrimal punctum 212, 214 or canaliculus 208, 210, to a sufficient diameter as the lacrimal implant 2500 is being implanted. In this way, the lacrimal implant 2500 can be implanted in various size ocular anatomies without the need for pre-dilation via a separate enlarging tool. In these examples, the integral dilator 2550 includes a generally concave shape related to the first portion 2504. In some examples, the concave shape includes a radius less than a radius of the canaliculus curvature 250. In some examples, the concave shape includes a radius substantially the same as the radius of the canaliculus curvature 250. As shown in the example of FIG. 25B, a smooth transition can exist between the first 2504 and second 2506 portions.

In certain examples, a proximal end 2528 of the second implant body portion 2506 can include a retention element 2556 configured to bias against at least a portion of a lacrimal canaliculus ampulla 252 (FIG. 2) when implanted. In the example of FIG. 25A, the retention element 2556 projects proximally from the intersection between the first 2504 and second 2506 implant body portions.

FIG. 26 illustrates an example of another lacrimal implant 2600 that is insertable through a lacrimal punctum 212, 214 and into the associated canaliculus 208, 210 (FIG. 2). In this example, the lacrimal implant 2600 comprises an implant body 2602 including first 2604 and second 2606 portions, and extends from a proximal end 2608 of the first portion 2604 to a distal end 2610 of the second portion 2606. The proximal end 2608 can define a longitudinal proximal axis 2612 and the distal end 2610 can define a longitudinal distal axis 2614. The implant body 2600 can be configured such that, when implanted, an angled intersection of between 90-135 degrees exists between the proximal axis 2612 and the distal axis 2614 for biasing at least a portion of the implant body against at least a portion of a lacrimal canaliculus 208, 210 located at or more distal to a canaliculus curvature 250 (FIG. 2).

In certain examples, the implant body 2602 can include a first cavity 2618 disposed near the proximal end 2608. In this example, the first cavity 2618 extends inward from the proximal end 2608 of the first portion 2604 to a position near the distal end 2610 of the second portion 2606. A first drug-releasing or other agent-releasing drug insert having a volume between about 0.2 cubic centimeters to about 0.25 cubic centimeters, for example, can be disposed in the first cavity 2618 to provide a extended sustained drug or other therapeutic agent release to an eye.

In certain examples, the second portion 2606 comprises an integral dilator 2650 to dilate anatomical tissue, such one or both of the lacrimal punctum 212, 214 or canaliculus 208, 210, to a sufficient diameter as the lacrimal implant 2600 is being implanted. In this way, the lacrimal implant 2600 can be implanted in various size ocular anatomies without the need for pre-dilation via a separate enlarging tool. In this example, the dilator 2650 includes a generally convex shape relative to the first portion 2604. In some examples, the convex shape includes a radius less than a radius of the canaliculus curvature 250. In some examples, the convex shape includes a radius substantially the same as the radius of the canaliculus curvature 250.

Figure 29:
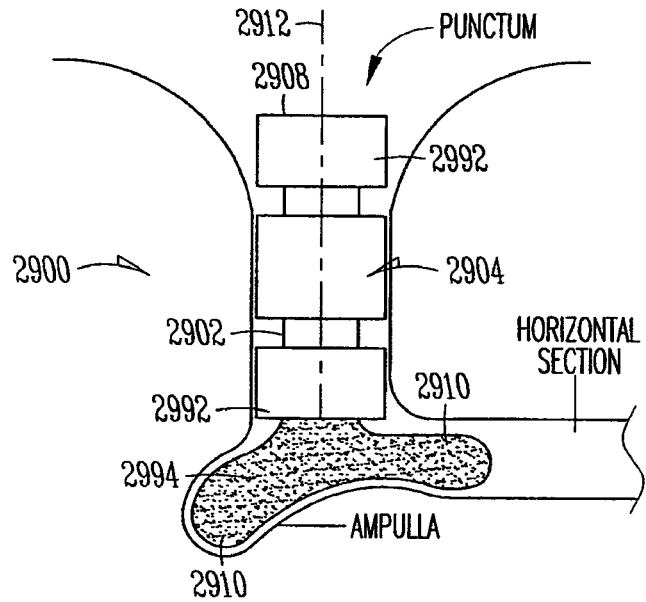
FIGS. 29-32 illustrate examples of a side view of various lacrimal implants configured to be retained within a lacrimal punctum and associated canalicular anatomy, each lacrimal implant including a fluid swellable retention element.
Figure 30:
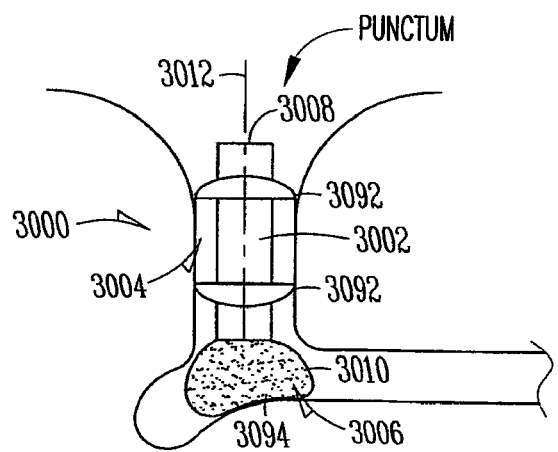
Figure 31:
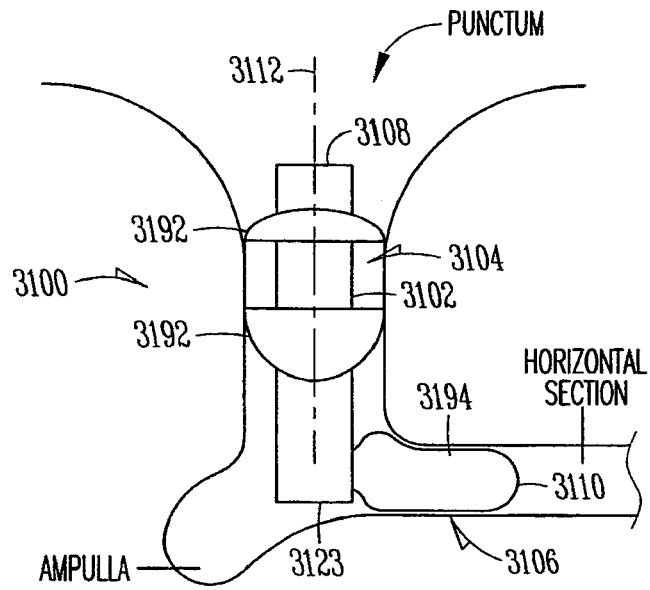
Figure 32:
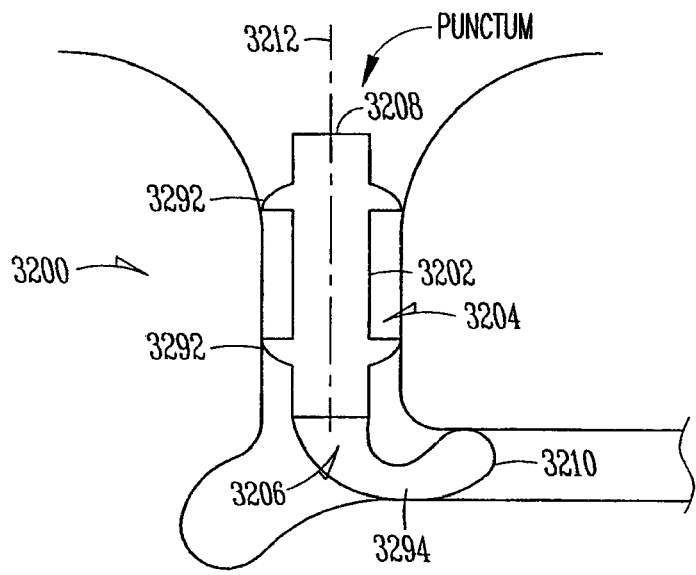

In certain examples, a proximal end 2628 of the second implant body portion 2606 can include a retention element 2656 configured to bias against at least a portion of a lacrimal canaliculus ampulla 252 (FIG. 2) when implanted. In this example, the retention element 2656 projects proximally from the intersection between the first 2604 and second 2606 implant body portions. In some examples, such as is shown in FIGS. 29-30, a proximal end 2628 of the second implant body portion 2606 can include a retention element 2656 comprising a hydrogel retention element, which is configured to expand into the ampulla 252 when the implant body 2602 is implanted.

Figure 27:
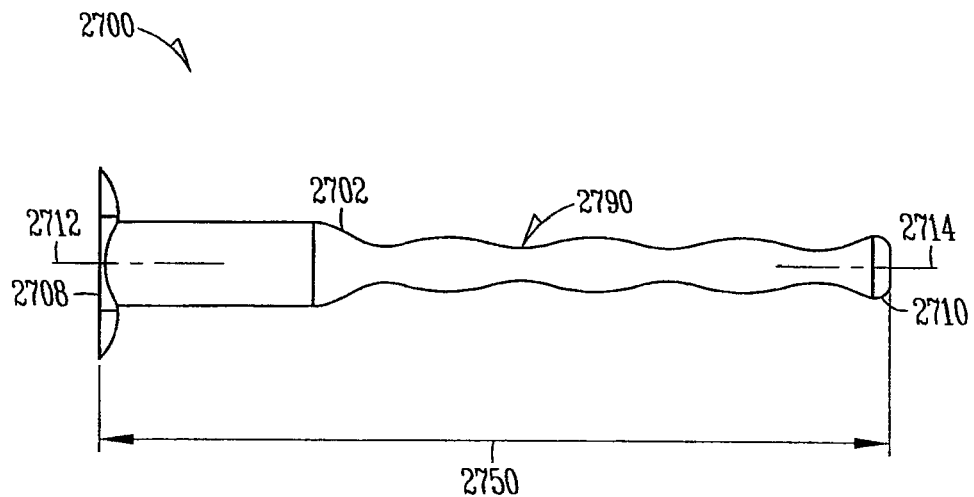
FIG. 27 illustrates an example of a side view of a lacrimal implant configured to be retained within a lacrimal punctum and associated canalicular anatomy, the lacrimal implant including an implant body portion having an undulating shape.

FIG. 27 illustrates an example of a side view of another lacrimal implant 2700 that is insertable through a lacrimal punctum 212, 214 and into the associated canaliculus 208, 210 (FIG. 2). In this example, the lacrimal implant 2700 comprises an implant body 2702 including first and second portions, which prior to implant, are linear relative to one another. The implant body 2702 extends from a proximal end 2708 of the first portion to a distal end 2710 of the second portion. The proximal end 2708 can define a longitudinal proximal axis 2712 and the distal end 2710 can define a longitudinal distal axis 2714. The implant body 2702 can be configured such that, when implanted, an angled intersection of between 45-135 degrees exists between the proximal axis 2712 and the distal axis 2714 such as for biasing at least a portion of the implant body 2702 against at least a portion of a lacrimal canaliculus 208, 210 (FIG. 2) located at or more distal to a canaliculus curvature 250 (FIG. 2). In this example, the second portion of the implant body 2702 includes at least one undulation 2790 to facilitate the biasing of the implant body 2702 against the portion of the lacrimal canaliculus 208, 210.

Figure 28:
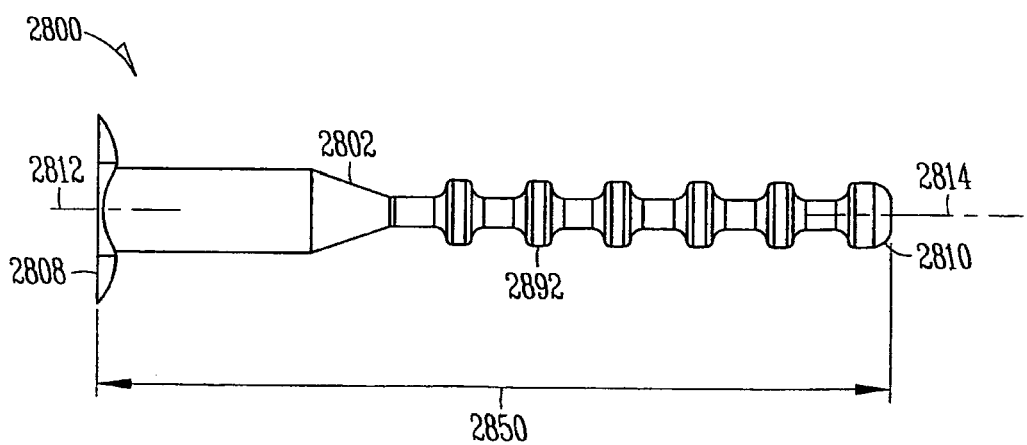
FIG. 28 illustrates an example of a side view of a lacrimal implant configured to be retained within a lacrimal punctum and associated canalicular anatomy, the lacrimal implant including at least one intermediately-disposed retainment projection.

FIG. 28 illustrates an example of a side view of another lacrimal implant 2800 that is insertable through a lacrimal punctum 212, 214 and into the associated canaliculus 208, 210 (FIG. 2). In this example, the lacrimal implant 2800 comprises an implant body 2802 including first and second portions, which prior to implant, are linear relative to one another. The implant body 2802 extends from a proximal end 2808 of the first portion to a distal end 2810 of the second portion. The proximal end 2808 can define a longitudinal proximal axis 2812 and the distal end 2810 can define a longitudinal distal axis 2814. The implant body 2802 can be configured such that, when implanted, an angled intersection of between 45-135 degrees exists between the proximal axis 2812 and the distal axis 2814 for biasing at least a portion of the implant body 2802 against at least a portion of a lacrimal canaliculus 208, 210 (FIG. 2) located at or more distal to a canaliculus curvature 250 (FIG. 2). In this example, the second portion of the implant body 2802 includes at least one intermediately-disposed retainment projection 2892, such an annular rib-like projection. The retainment projection 2892 includes a cross-sectional size greater than an adjacent implant body portion and can facilitate the securement of an implanted position of the implant body 2802, while the adjacent narrower implant body portion can facilitate the biasing of the implant body 2802 against the portion of the lacrimal canaliculus 208, 210.

FIGS. 29-32 illustrate examples of a side view of other lacrimal implants 2900, 3000, 3100, 3200 that are insertable through a lacrimal punctum 212, 214 and into the associated canaliculus 208, 210 (FIG. 2). In these examples, each lacrimal implant 2900, 3000, 3100, 3200 can comprise an implant body 2902, 3002, 3102, 3202 including first 2904, 3004, 3104, 3204 and second 2906, 3006, 3106, 3206 portions, and can extend from a proximal end 2908, 3008, 3108, 3208 of the first portion 2904, 3004, 3104, 3204 to a distal end 2910, 3010, 3110, 3210 of the second portion 2906, 3006, 3106, 3206. The proximal end 2908, 3008, 3108, 3208 can define a longitudinal proximal axis 2912, 3012, 3112, 3212.

The second portion 2906, 3006, 3106, 3206 can include a fluid swellable retention element 2994, 3094, 3194, 3294 configured to expand laterally, relative to the proximal axis 2912, 3012, 3112, 3212, when the implant body 2902, 3002, 3102, 3202 is implanted. In various examples, the fluid swellable retention element 2994, 3094, 3194, 3294 can be formed such that one or both of expansion direction or expansion amount can be controlled. For instance, the fluid swellable retention element 2994, 3094, 3194, 3294 can expand more in one plane than another to securely anchor the lacrimal implants. In some examples, the fluid swellable retention element 2994, 3094, 3194, 3294 includes a portion configured to expand laterally, relative to the proximal axis 2912, 3012, 3112, 3212, in a direction away from a lacrimal canaliculus ampulla 252 (FIG. 2) when the implant body is implanted. In some examples, as shown in FIGS. 29-30, the fluid swellable retention element 2994, 3094, 3194, 3294 includes a portion configured to expand laterally, relative to the proximal axis 2912, 3012, 3112, 3212, in a direction toward the lacrimal canaliculus ampulla 252 (FIG. 2) when the implant body is implanted.

In some examples, the fluid swellable retention element 2994, 3094, 3194, 3294 can comprise hydrogel, which is insertable through the lacrimal punctum 212, 214 and into the associated canaliculus 208, 210 in a narrow profile. After insertion, the hydrogel or other fluid swellable retention element can hydrate and expand to a wide configuration. Protrusions, such as at least one intermediately-disposed retainment projection 2992, 3092, 3192, 3292, can be used to retain to an implanted position of the lacrimal implants while the hydrogel or other swellable element expands.

Figure 33:
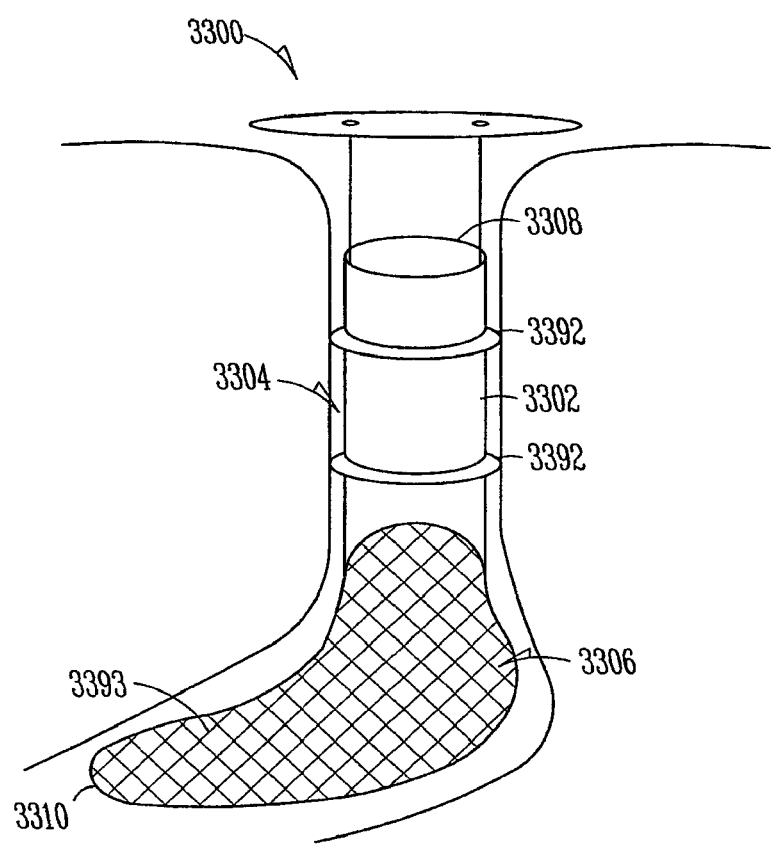
FIG. 33 illustrates an example of a side view of a lacrimal implant configured to be retained within a lacrimal punctum and associated canalicular anatomy, the lacrimal implant including an expandable retention element.

FIG. 33 illustrates an example of a side view of another lacrimal implant 3300 that is insertable through a lacrimal punctum 212, 214 and into the associated canaliculus 208, 210 (FIG. 2). In this example, the lacrimal implant 3300 can comprise an implant body 3302 including first 3304 and second 3306 portions, and can extend from a proximal end 3308 of the first portion 3304 to a distal end 3310 of the second portion 3306. As shown, the second portion 3306 can include an expandable retention element 3393 comprising at least one of a coil, a braid, a stent, a mesh tube, a suture, a thermoset polymer, a thermoplastic, a heat activatable material, or a shape memory material. The expandable retention element 3393 can be configured to expand laterally, relative to a proximal axis 3312 defined by the first portion 3304, when the implant body is implanted. Protrusions, such as at least one intermediately-disposed retainment projection 3392, can be used to potentially further secure an implanted position of the lacrimal implant.

FIGS. 34A-34B illustrate examples of a schematic view of another lacrimal implant 3400 and an implant environment. In various examples, the implant body 3402 can include a graspable or other projection 3432, such as one or more projections extending laterally at least partially from or around a proximal end 3408 of a first implant body portion. In some examples, such as is shown in FIG. 34B, the projections 3432 can include a set of wings for use in inserting the lacrimal implant 3400 into, or removing the implant from, an implanted position. The set of wings can be configured without migration in mind, as the implanted, non-linear configuration of the implant body 3402 can prevent migration by assuming a size or shape of a canaliculus curvature 250 and optionally, a lacrimal canaliculus ampulla 252.

In the examples of FIGS. 34A-34B, the one or more projections 3432 extend laterally in a direction parallel to or away from an eye 100 when implanted. In this way, the projections 3432 can still act as a graspable or feedback feature, but can limit patient discomfort when the lacrimal implant 3400 is implanted. In addition, the projections 3432, by extending away from the eye 100, may not be buried in tissue and may be easily recognized by the patient or physician. This can allow for a quick determination if the lacrimal implant 3400 is being retained in its proper place without having to dig and search in the soft tissue surrounding the eye 100. In some instances, a simple pull on the lower eyelid can expose the projection 3432 pointed in a direction away from the eye 100. In the example of FIG. 34B, a lateral extension of at least one projection 3432 from the proximal end 3408 is substantially the same as a lateral extension direction of a second implant body portion relative to a distal end of the first implant body portion.

FIGS. 35-38 illustrate examples of an isometric view of various graspable projections or other gripping means 3532, 3632, 3732, 3832 extending from a proximal end of a lacrimal implant 3500, 3600, 3700, 3800. The graspable or other projections 3532, 3632, 3732, 3832 can be used for various functions, including providing a structure to which a user can grasp onto during implant insertion or removal, inhibiting or preventing the associated lacrimal implant from passing completely within a lacrimal punctum 212, 214 and associated canaliculus 208, 210 (FIG. 2), or for providing tactile or visual feedback information to the user, e.g., as to whether the implant is fully implanted.

Figure 35:
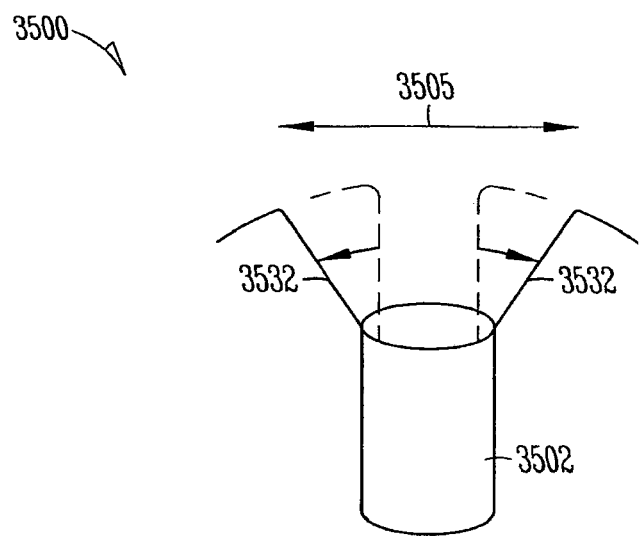
FIGS. 35-38 illustrate examples of an isometric view of various lacrimal implant proximal end portions, each proximal end portion including a graspable projection or void.

In some examples, as shown in FIG. 35, the graspable projection 3532 can include two or more expandable arm members, which are sized to rest on an exterior of the lacrimal punctum. The arm members can be affixed to an implant body 3502, for example, via molding, adhesion or welding. The expandable arm members are capable of expanding so as to limit penetration of the lacrimal implant 3500 through the lacrimal punctum 212, 214 and into the associated canaliculus 208, 210. While two arm members are shown, some include more than two arm members, such as four arm members. The expandable arm members can assume an expanded profile separation distance 3505 that corresponds to about twice a diameter of the implant body, such that proximal ends of the proximal expandable arm members remain on the exterior of the punctum. The expandable arm members can expand in many ways from the narrow profile configuration to the expanded profile configuration, and can include at least one of a coil, a braid, a suture, a thermoset polymer, a thermoplastic, a heat activated material, Nitinol, a shape memory material, a polymer, polypropylene, polyester, nylon, natural fibers, stainless steel, polymethylmethacrylate or polyimide. In some examples, the expandable arm members can be expanded manually, for example by a physician, after the lacrimal implant has been positioned in the canalicular lumen 208, 210.

Figure 36:
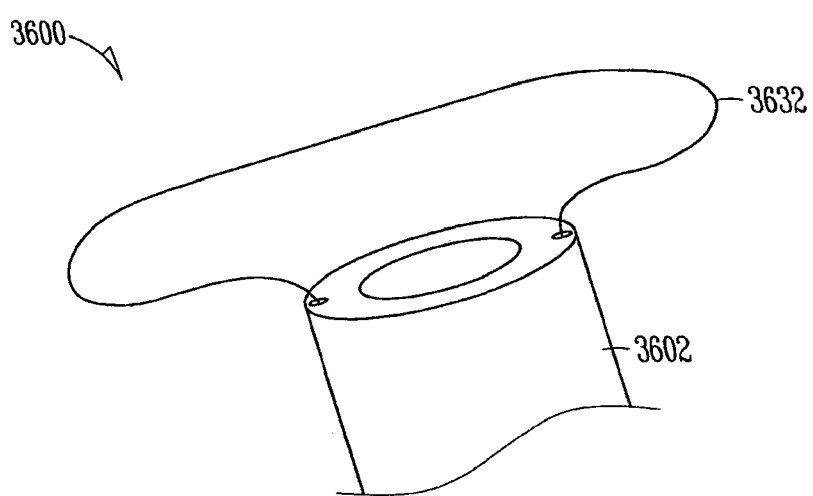

In some examples, as shown in FIG. 36, the graspable projection 3632 can include a loop of a filament embedded in the proximal end of the lacrimal implant 3600 to permit removal of the implant with proximal tension to the loop, for example with forceps. In some examples, the loop of filament assumes a shape similar to a purse handle that extends from the lacrimal implant with a loop so as to facilitate removal of the lacrimal implant. The filament can comprise at least one of a heat activated material, Nitinol, a shape memory material, a polymer, polypropylene, polyester, nylon, natural fibers, stainless steel, polymethylmethacrylate or polyimide. In some embodiments, the filament may comprise an absorbable thermo plastic polymer, for example at least one of polylactic acid (PLA), poly glycolic acid (PGA) or polylactic co-glycolic acid (PLGA). A distal end of the filament can be embedded in, molded to or otherwise affixed to an implant body 3602 so as to secure the filament to the lacrimal implant.

Figure 37:
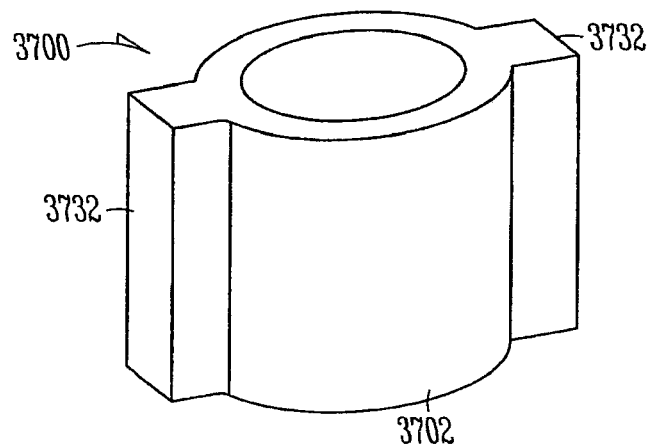

In some examples, as shown in FIG. 37, the graspable projection 3732 can include at least one axially extending projection coupled with an implant body 3702, which is configured to bias an outer most portion of the lacrimal canaliculus 208, 210. Due to the natural constriction against outward biasing of the canaliculus, the interplay between the axially extending projections and the canaliculus inhibits over insertion of an associated lacrimal implant 3700.

Figure 38:
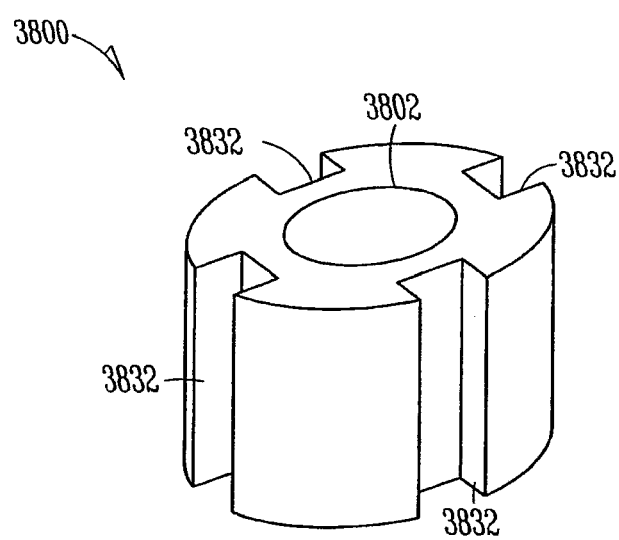

In some examples, as shown in FIG. 38, a longitudinal indentation, channel or other recess 3832 in an implant body 3802 can be used in lieu of a graspable projection to permit insertion or removal of a lacrimal implant 3800. The indentation, channel or other recess 3832 may extend axially along only a portion of an implant body a sufficient distance to facilitate removal of an associated lacrimal implant. In further examples, a lacrimal implant can include a filament molded into an implant body and extending proximally for removal of the implant from the punctum.

Figure 39A:
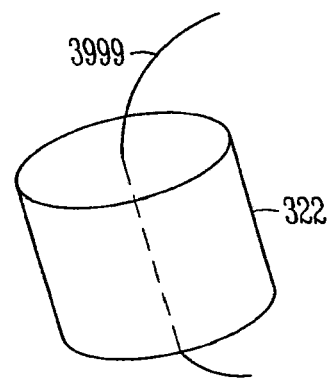
FIGS. 39A-39B illustrate examples of an isometric view of drug inserts and a removal-facilitating filament.
Figure 39B:
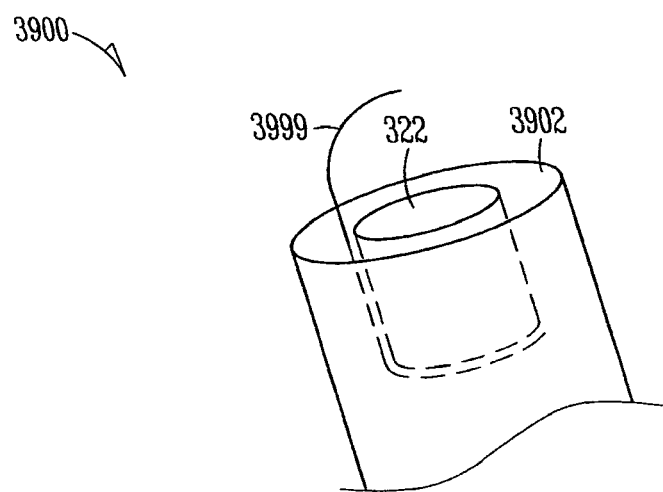

FIGS. 39A-39B illustrate examples of an isometric view of a drug insert 322 and a removal facilitating filament 3999. In some examples, as shown in FIG. 39A, the filament 3999 can extend from the drug insert 322 and is molded therein for removal purposes. Among other things, the filament 3999 can comprise a suture, a thermoset polymer, or a shape memory alloy. In some examples, as shown in FIG. 39B, the filament 3999 extends along the drug insert 322 adjacent an implant body 3902 and is bonded to a distal end of the insert for removal purposes. Filament can be bonded to the distal end of the drug core insert with an adhesive, such as cyanoacrylate, acrylic, epoxy, urethane or a hot melt adhesive.

Figure 40:
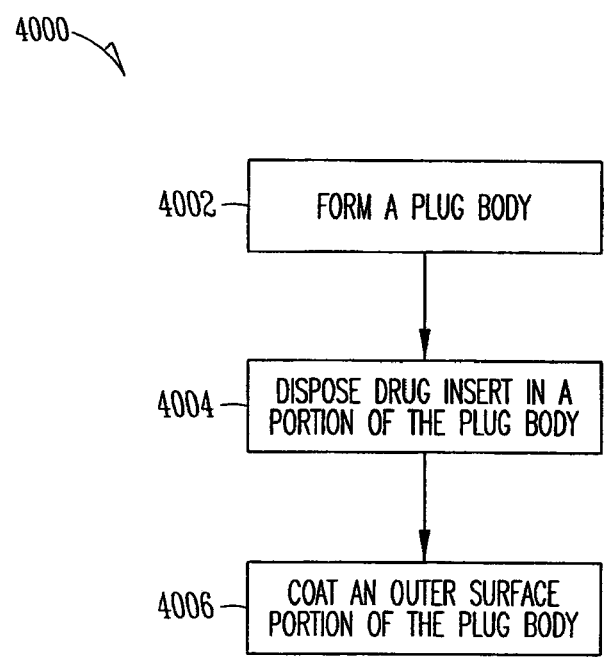
FIG. 40 illustrates an example of a method of manufacturing a lacrimal implant configured to be retained within a lacrimal punctum and associated canalicular anatomy.

FIG. 40 is a block diagram illustrating an example of a method 4000 of manufacturing a lacrimal implant configured to be at least partially insertable through a lacrimal punctum and into the associated canaliculus. At 4002, an implant body extending from a proximal end of a first body portion to a distal end of a second body portion is formed.

In some examples, various sizes of implant bodies are formed to fit various patient anatomies. In various examples, the proximal end is formed to define a longitudinal proximal axis and the distal end is formed to define a longitudinal distal axis. A formation of the implant body can be configured such that, when implanted, the proximal axis and the distal axis intersect at an angle of at least 45 degrees to laterally bias at least a portion of the implant body against at least a portion of a lacrimal canaliculus located at or more distal to a canaliculus curvature.

In some examples, the second body portion is formed to include a dilator generally narrowing from a location near a proximal end of the second body portion to the distal end of the second body portion. In some examples, the dilator is formed by sloping an outer surface of the second portion of the implant body between about 1 degree and about 10 degrees with respect to the longitudinal distal axis. In some examples, the outer surface of the second implant body portion is sloped to a dilator tip of between about 0.2 millimeters and about 0.5 millimeters.

In some examples, the implant body is formed to include a graspable or other projection extending laterally from the proximal end of the first body portion. In certain examples, the projection is formed to substantially align with a lateral extension direction of the second body portion relative to the first body portion. In certain examples, the projection is formed such that, when implanted, it laterally extends from the proximal end of the first body portion in a direction that is parallel to or away from an eye.

At 4004, a drug insert is disposed in at least one of the first body portion or the second body portion. In various examples, the drug insert is positioned such that an exposed drug insert surface sits adjacent at least one of the proximal end or the distal end for providing a sustained drug or other therapeutic agent release to an eye, nasal passage or inner ear, for example. In certain examples, a first drug insert is disposed in the first body portion and a second drug insert is disposed in the second body portion. In various examples, the one or more drug inserts comprise drug cores including the drug or other therapeutic agent.

At 4006, an outer surface portion of the implant body is coated with at least one of a fluid swellable material, a lubricious coating or an antimicrobial coating. In various examples, the outer surface portion of the implant body is polished using a polishing process.

Sheath Body Examples:

In various ways, the sheath body can comprise appropriate shapes and materials to control migration of drug or other therapeutic agents from a drug insert. In some examples, the sheath body is configured to be conformable to an implant anatomy, such as an anatomy of a lacrimal punctum or associated canaliculus. As discussed, in some examples, the sheath body at least partially covers or surrounds the drug insert and can fit snugly against an outer surface of a matrix/agent mixture. The sheath body can be made from a material that is substantially impermeable to the drug or other therapeutic agent so that the rate of migration of the drug or agent is largely controlled by an exposed surface area of the drug insert that is not covered by the sheath body. In many examples, migration of the agents through the sheath body can be about one tenth of the migration of the agent through the exposed surface of the drug insert, or less. Suitable sheath body materials can include, among others, polyimide, polyethylene terephthalate (PET). The sheath body can have a thickness, as defined from the sheath surface adjacent the outer matrix/agent mixture surface to an opposing sheath surface away from the outer surface, of about 0.00025 inches to about 0.0015 inches. The total diameter of the sheath that extends across the drug insert ranges from about 0.2 millimeters to about 1.2 millimeters. The drug insert can be formed by dip coating the matrix in the sheath body. In some examples, the sheath body can comprise a tube into which the matrix/agent mixture is introduced. The sheath body can also be dip coated around the matrix/agent mixture, for example dip coated around a pre-formed matrix/agent core.

The sheath body can be provided with one or more additional features such as to facilitate clinical use of the lacrimal implants discussed herein. For example, the sheath can receive a drug insert that is exchangeable in situ, while the implant body remains implanted in the patient, or after its removal. In some examples, the sheath body can be provided with one or more external protrusions that apply force to the sheath body when squeezed, which cause the matrix/agent mixture to be ejected from the sheath body. A replacement drug insert can then be positioned in the sheath body.

Therapeutic Agent Examples:

A therapeutic agent (or simply "agent") can comprise, among other things, a drug made from one or any combination of the following or their equivalents, derivatives or analogs, including, anti-glaucoma medications, (e.g. adrenergic agonists, adrenergic antagonists (beta blockers), carbonic anhydrase inhibitors (CAIS, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Example available agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present lacrimal implants, include triamcinolone acetonide (generic name) and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens, —estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present lacrimal implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdata.fda.gov/scripts/cder/drugsatfda/index. The present lacrimal implants can also be used with drugs listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Examples of diseases or disorders that can be treated with above-listed agents include, but are not limited to, glaucoma, pre- and post-surgical ocular treatments, dry eye, anti-eye allergy, anti-infective, post-surgical inflammation or pain, respiration-related disorders, such as allergies, inner ear disorders, such as dizziness or migraines, or other systemic disorders, such as hypertension, cholesterol management, pulmonary disorders or immunological disorders. In some examples, the therapeutic agent can include a lubricant or a surfactant, for example a lubricant to treat dry eye. In other examples, the therapeutic agent can include an absorbent capable of absorbing tear from an eye.

Drug Insert Examples:

The drug insert can comprise one or more drugs or other therapeutic agents, and in some examples, one or more matrix materials to provide sustained release of the drug or other agents. The one or more drugs or other therapeutic agents can migrate from an exposed surface of the drug insert to the target tissue (e.g., ciliary muscles of an eye) based, at least in part, on a solubility of the drugs or agents in the matrix. The rate of migration of the drugs or agents from the exposed surface can also be related to the concentration of drugs or agents dissolved in the matrix. In some examples, the concentration of drugs or agents dissolved in the drug insert can be controlled to provide the desired release rate of the drugs or agents. In addition or in combination, the rate of migration of drugs or agents from the exposed surface can be related to one or more properties of the matrix in which the drugs or agents dissolve, such as the properties of a silicone matrix formulation. In some examples, the drugs or agents included in the drug insert can include liquid, solid, solid gel, solid crystalline, solid amorphous, solid particulate, or dissolved forms. In one such example, liquid Latanoprost droplets or solid Bimatoprost particles are dispersed in a silicone matrix.

The drug insert can comprise one or more biocompatible materials capable of providing a sustained release of the one or more drugs or agents. Although the drug insert is primarily discussed above with respect to an example comprising a matrix including a substantially non-biodegradable silicone matrix with dissolvable inclusions of the drugs or agents located therein, the drug insert can include other structures that provide sustained release of the drugs or agents, for example a biodegradable matrix, a porous drug insert, a liquid drug insert or a solid drug insert. A matrix that includes the drugs or agents can be formed from either biodegradable or non-biodegradable polymers. In some examples, a non-biodegradable drug insert can include silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some examples, a biodegradable drug insert can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug insert can comprise a hydrogel polymer.

CLOSING NOTES

Among other things, lacrimal implants and related methods providing secure retention within a lacrimal punctum and canaliculus of an eye are discussed herein. The lacrimal implants can comprise an implant body configured for at least partial insertion through the lacrimal punctum and into the canaliculus. The implant body can include first and second portions, and can extend from a proximal end of the first portion defining a longitudinal proximal axis to a distal end of the second portion defining a longitudinal distal axis. The implant body can be configured such that, when implanted using an integral dilator, an at least 45 degree angled intersection exists between the proximal axis and the distal axis. In this way, at least a portion of the implant body can be biased against at least a portion of the lacrimal canaliculus located at or more distal to a canalicular curvature, thereby retaining an implanted position of the lacrimal implant using anatomical structures. In various examples, the lacrimal implant can further comprise a drug insert disposed in at least one of the first portion or the second portion of the implant body to provide a sustained release of a drug or other therapeutic agent to an eye, nasal passage, or inner ear system, for instance.

Advantageously, in some examples, the present lacrimal implants can successfully block the flow of tears or provide sustained delivery of a drug or other therapeutic agent to an eye, nasal passage, or inner ear for varying periods of time, such as from days to months to years. In addition, by including first and second implant body cavities, a dual drug or other agent releasing profile can be possible. For instance, two separate drugs can be released from two different implant locations. Further, the canalicular curve retaining configuration of the present implant body can reduce overstretching of the lacrimal punctum and canaliculus and inadvertent fall out of implants. Even further, it is believe the present lacrimal implants can be implemented so as to provide a one-size-fits-all (or many) regime, as an expandable coating or other expandable retention member can be applied to the implant body, such as an outer surface portion of the implant body, to fit in hollow tissue structures of varying sizes. The present lacrimal implant may also be better tolerated by a patient due to, for example, an orientation of a graspable or other projection located at the proximal end of the implant body.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable Inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the term "about" is used to refer to an amount that is approximately, nearly, almost, or in the vicinity of being equal to a stated amount.

In this document, the term "proximal" refers to a location relatively closer to a hand of a physician implanting a lacrimal implant into a patient, and the term "distal" refers to a location relatively further from the hand of the physician, particularly during the implanting of the implant into the patient.

In this document, the term "hydrogel" is used to refer to an absorbing or otherwise retaining material (e.g., adsorbing material), such as super-absorbent polymers, hydrocolloids, and water-absorbent hydrophilic polymers, for example. In some examples, the term "hydrogel" refers to super-absorbent polymer particles in a "dry" state, more specifically, particles containing from no water up to an amount of water less than the weight of the particles, such as less than about 5%, by weight, water. In some examples, the term "hydrogel" refers to a super-absorbent polymer in the "dry" state when the hydrogel is not expandable and also refers to its hydrated or expanded state, more specifically, hydrogels that have absorbed at least their weight in water, such as several times their weight in water. As the hydrogel material absorbs fluid, its size can increase (swell) and its shape can change to bias against at least a portion of a lacrimal canaliculus ampulla or lacrimal canaliculus wall, for example.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) can be used in combination with each other. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A kit for implanting a lacrimal implant into a lacrimal canaliculus, comprising:
    an insertion tool; and,
    a lacrimal implant comprising an implant body, comprising a first and second portions, the implant body non-linearly extending from a proximal end portion positionable within a vertical section of the lacrimal canaliculus to a distal end portion positionable within a horizontal section of the lacrimal canaliculus and having an intermediate portion therebetween, the proximal end of the first portion defining a longitudinal proximal axis and the distal end of the second portion defining a longitudinal distal axis, the first portion including a cavity;
    a therapeutic agent disposed in the cavity;
    the intermediate portion partially extending in a first direction toward the proximal end portion, partially extending in a second direction toward the distal end portion, and partially extending in a third direction along the longitudinal distal axis, configured to bias against a portion of a lacrimal canaliculus ampulla wherein the third direction is perpendicular to the first direction of the intermediate portion, such that, when implanted in the lacrimal canaliculus, the implant body directionally biases laterally against at least a portion of the lacrimal canaliculus located at or more distal to a canalicular curvature.

2. The kit of claim 1, wherein the therapeutic agent is selected from the group consisting of thrombin inhibitors; antithrombogenic agents; thrombolytic agents; fibrinolytic agents; vasospasm inhibitors; vasodilators; antihypertensive agents; antimicrobial agents; antibiotic agents; antifungal agents; antiviral agents; inhibitors of surface glycoprotein receptors; antiplatelet agents; antimitotics; microtubule inhibitors; anti-secretory agents; active inhibitors; remodeling inhibitors; antisense nucleotides; anti-metabolites; anti-proliferatives; anticancer chemotherapeutic agents; anti-inflammatories; non-steroidal anti-inflammatories (NSAIDs); prostaglandins, prostaglandin analogues, antiprostaglandins, prostaglandin precursors, acetazolamide, dorzolamide, brinzolamide, methazolamide, dichlorphenamide, diamox; lubezole, nimodipine, pilocarpine, carbachol, physostigmine and combinations thereof.

3. The kit of claim 1, wherein the therapeutic agent is a glaucoma drug selected from Timolol, betaxolol, levobunolol, atenolol, bimatoprost, travoprost, and latanoprost.

4. The kit of claim 1, wherein the therapeutic agent is dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

5. The kit of claim 1, wherein the therapeutic agent treats at least one of glaucoma, pre- and post-surgical ocular indications, dry eye, eye allergy symptoms, ocular infection, or post-surgical inflammation or pain.

6. The kit of claim 1, wherein the implant body comprises silicone.

7. The kit of claim 1, wherein a drug insert comprising the therapeutic agent is disposed in the cavity.

8. The kit of claim 7, wherein the drug insert comprises a matrix and a sheath body disposed over at least a portion of the matrix and therapeutic agent to define at least one insert exposed surface located at or near the proximal end of the first portion implant body.

9. The kit of claim 8, wherein the matrix comprises silicone, acrylates, polyethylenes, polyurethane, polyurethane, hydrogel, polyester, polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy, titanium, stainless steel, cobalt-chrome alloy, protein, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) or combinations thereof.

10. The kit of claim 1, wherein the implant body is configured such that an angled intersection exists between the proximal axis and the distal axis prior to being implanted in the lacrimal canaliculus.

11. The kit of claim 10, wherein the angled intersection is between 45 degrees and 135 degrees.

12. The kit of claim 1, wherein the second portion includes an integral dilator, the integral dilator generally narrowing from a location near a proximal end of the second portion to the distal end of the second portion to facilitate implantation of the implant body into the lacrimal canaliculus.

13. The kit of claim 12, wherein a diameter of an integral dilator tip is between about 0.2 millimeters and about 0.5 millimeters.

14. The kit of claim 1, wherein the implant body comprises a graspable projection extending at least partially from the proximal end of the first portion, the graspable projection configured to seat against or near a lacrimal punctum when the implant body is implanted.

15. A kit for insertion of a lacrimal implant into a lacrimal canaliculus, comprising:
an insertion tool; and,
a lacrimal implant comprising an implant body, including first and second portions, the implant body extending from a proximal end of the first portion to a distal end of the second portion, the first portion including a cavity;
a therapeutic agent disposed in the cavity;
the proximal end of the first portion defining a longitudinal proximal axis and the distal end of the second portion defining a longitudinal distal axis and wherein the second portion includes an element extending or expanding laterally into a lacrimal canaliculus ampulla when the implant body is implanted;
the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature; and
wherein the second portion of the implant body includes a longitudinal length having a magnitude less than four times a longitudinal length of the first portion of the implant body.

16. The kit of claim 15, wherein the therapeutic agent is selected from the group consisting of thrombin inhibitors; antithrombogenic agents; thrombolytic agents; fibrinolytic agents; vasospasm inhibitors; vasodilators; antihypertensive agents; antimicrobial agents; antibiotic agents; antifungal agents; antiviral agents; inhibitors of surface glycoprotein receptors; antiplatelet agents; antimitotics; microtubule inhibitors; anti-secretory agents; active inhibitors; remodeling inhibitors; antisense nucleotides; anti-metabolites; anti-proliferatives; anticancer chemotherapeutic agents; anti-inflammatories; non-steroidal anti-inflammatories (NSAID s); prostaglandins, prostaglandin analogues, antiprostaglandins, prostaglandin precursors, acetazolamide, dorzolamide, brinzolamide, methazolamide, dichlorphenamide, diamox; lubezole, nimodipine, pilocarpine, carbachol, physostigmine and combinations thereof.

17. The kit of claim 15, wherein the therapeutic agent is a glaucoma drug selected from Timolol, betaxolol, levobunolol, atenolol, bimatoprost, travoprost, latanoprost, dorzolamide. olopatadine, cyclosporin, brimonidine, moxifloxacin, tobramycin, brinzolamide, aciclovir timolol maie, ate, ketorolac tromethamine, prednisolone acetate, sodium hyaluronate, nepafenac, bromfenac, diclofenac, flurbiprofen, suprofenac, binoxan, paianol. dexamethasoneltobrainycin combination, moxifloxacin, or acyclovir.

18. The kit of claim 15, wherein the therapeutic agent treats at least one of glaucoma, pre- and post-surgical ocular indications, dry eye, eye allergy symptoms, ocular infection, or post-surgical inflammation or pain.

19. A kit for insertion of a lacrimal implant into a lacrimal canaliculus, comprising:
   an insertion tool; and,
   a lacrimal implant comprising an implant body, including first and second portions, the implant body extending from a proximal end of the first portion to a distal end of the second portion, the first portion including a cavity;
   a therapeutic agent disposed in the cavity;
   the proximal end of the first portion defining a longitudinal proximal axis and the distal end of the second portion defining a longitudinal distal axis and wherein the second portion includes an element extending or expanding laterally into a lacrimal canaliculus ampulla when the implant body is implanted; and,
   the implant body configured such that, when implanted in the lacrimal canaliculus, an angled intersection exists between the proximal axis and the distal axis for biasing at least a portion of the implant body against at least a portion of the lacrimal canaliculus located at or more distal to a canalicular curvature.

\* \* \* \* \*